(12) United States Patent
Bauernschmitt et al.

(10) Patent No.: US 12,241,764 B2
(45) Date of Patent: Mar. 4, 2025

(54) METHOD AND DEVICE FOR NON-INVASIVELY DETERMINING PROPERTIES OF A MULTIPHASE FLOW

(71) Applicant: ROSEN SWISS AG, Stans (CH)

(72) Inventors: Rüdiger Bauernschmitt, Linkenheim-Hochstetten (DE); Michael Black, Münster (DE); Natalia Rodriguez, CR Enschede (NL); Ralf Schlesiger, Münster (DE); Burkhard Reetmeyer, Neuenhaus (DE)

(73) Assignee: ROSEN 2 Holding AG, Stans (CH)

( * ) Notice: Subject to any disclaimer, the term of this patent is extended or adjusted under 35 U.S.C. 154(b) by 616 days.

(21) Appl. No.: 17/285,934

(22) PCT Filed: Oct. 10, 2019

(86) PCT No.: PCT/EP2019/077533
§ 371 (c)(1),
(2) Date: Apr. 16, 2021

(87) PCT Pub. No.: WO2020/078833
PCT Pub. Date: Apr. 23, 2020

(65) Prior Publication Data
US 2021/0381866 A1 Dec. 9, 2021

(30) Foreign Application Priority Data
Oct. 18, 2018 (DE) .......................... 102018125923.9

(51) Int. Cl.
*G01F 1/663* (2022.01)
*G01N 29/032* (2006.01)
(Continued)

(52) U.S. Cl.
CPC .......... *G01F 1/663* (2013.01); *G01N 29/032* (2013.01); *G01N 29/222* (2013.01);
(Continued)

(58) Field of Classification Search
CPC .... G01F 1/663; G01N 29/032; G01N 29/222; G01N 29/2412; G01N 33/2847;
(Continued)

(56) References Cited

U.S. PATENT DOCUMENTS

| 5,929,342 A | 7/1999 | Thompson |
| 6,369,881 B1 * | 4/2002 | Wang .................... G01F 1/7086 356/28 |

(Continued)

FOREIGN PATENT DOCUMENTS

| DE | 102009022492 A1 | 12/2010 |
| DE | 102012019217 A1 | 4/2014 |

(Continued)

OTHER PUBLICATIONS

Akinori Furusawa et al. "Mode control of guided wave in magnetic hollow cylinder using electromagnetic acoustic transducer array", Nuclear Engineering and Technology, vol. 47, No. 2, Mar. 1, 2015 (Mar. 1, 2015), pp. 196-203, DOI: 10.1016/j.net.2014.12.007, ISSN: 1738-5733, XP055686046.

(Continued)

*Primary Examiner* — Tarun Sinha
(74) *Attorney, Agent, or Firm* — Husch Blackwell LLP

(57) ABSTRACT

A method is provided for non-invasively determining properties of a multiphase flow which flows through an electrically conductive object. Using a single set-up having a plurality of EMAT transducers, at least one property of the multiphase flow is determined by means of at least one of a plurality of measurement methods. A device is also provided for non-invasively determining properties of a multiphase flow which flows through an electrically conductive object. At least four EMAT transducers are positionable upstream along a first object cross-section at or near the object wall and at least four EMAT transducers are positionable down- (Continued)

stream along a second object cross-section at or near the object wall.

37 Claims, 17 Drawing Sheets

(51) Int. Cl.
*G01N 29/22* (2006.01)
*G01N 29/24* (2006.01)
*G01N 33/28* (2006.01)

(52) U.S. Cl.
CPC ..... *G01N 29/2412* (2013.01); *G01N 33/2847* (2013.01); *G01N 2291/015* (2013.01); *G01N 2291/024* (2013.01); *G01N 2291/106* (2013.01)

(58) Field of Classification Search
CPC ....... G01N 2291/015; G01N 2291/024; G01N 2291/106; G01N 29/024; G01N 2291/017; G01N 2291/02433; G01N 2291/02836; G01N 2291/0289; G01N 2291/0425; G01N 2291/044; G01N 2291/2634; G01P 5/241
See application file for complete search history.

(56) References Cited

U.S. PATENT DOCUMENTS

| | | |
|---|---|---|
| 6,575,043 B1 | 6/2003 | Huang et al. |
| 2003/0033870 A1 | 2/2003 | Shah et al. |
| 2015/0260561 A1 | 9/2015 | Twerdowski et al. |
| 2018/0010941 A1 | 1/2018 | Baumoel |
| 2020/0088686 A1* | 3/2020 | Sinha ................. G01N 29/348 |

FOREIGN PATENT DOCUMENTS

| | | |
|---|---|---|
| EP | 1081465 A2 | 3/2001 |
| EP | 2913641 A2 | 9/2015 |
| JP | 2000097742 A | 4/2000 |
| WO | 0003207 A1 | 1/2000 |
| WO | 2002077635 A2 | 10/2002 |
| WO | 2011078691 A2 | 6/2011 |
| WO | 2018175503 A2 | 9/2018 |

OTHER PUBLICATIONS

Edwards, R. S.; Dixon, S.; Jian, X. Non contact ultrasonic-characterization of defects using EMATs. In: AIP Conference Proceedings. AIP, 2005. S. 1568-1575.

Marc Seeger, von ROSEN Technology AG: "ROSEN EMAT Flowmeter", Präsentation auf der Messe "Instrumentatie und Analyse, Dagen 2017", in Vianen, Niederlande, Jun. 21, 2017.

* cited by examiner

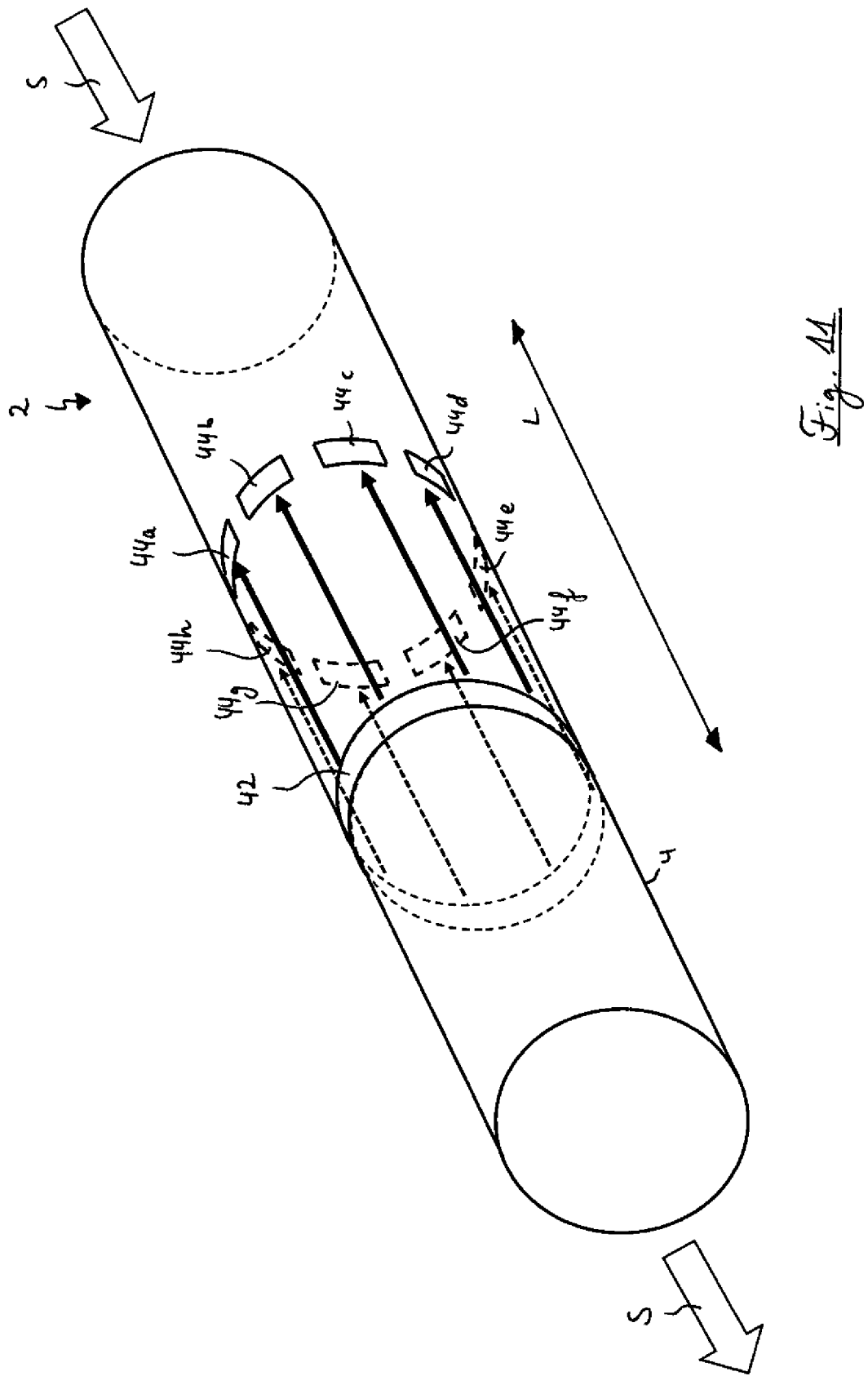

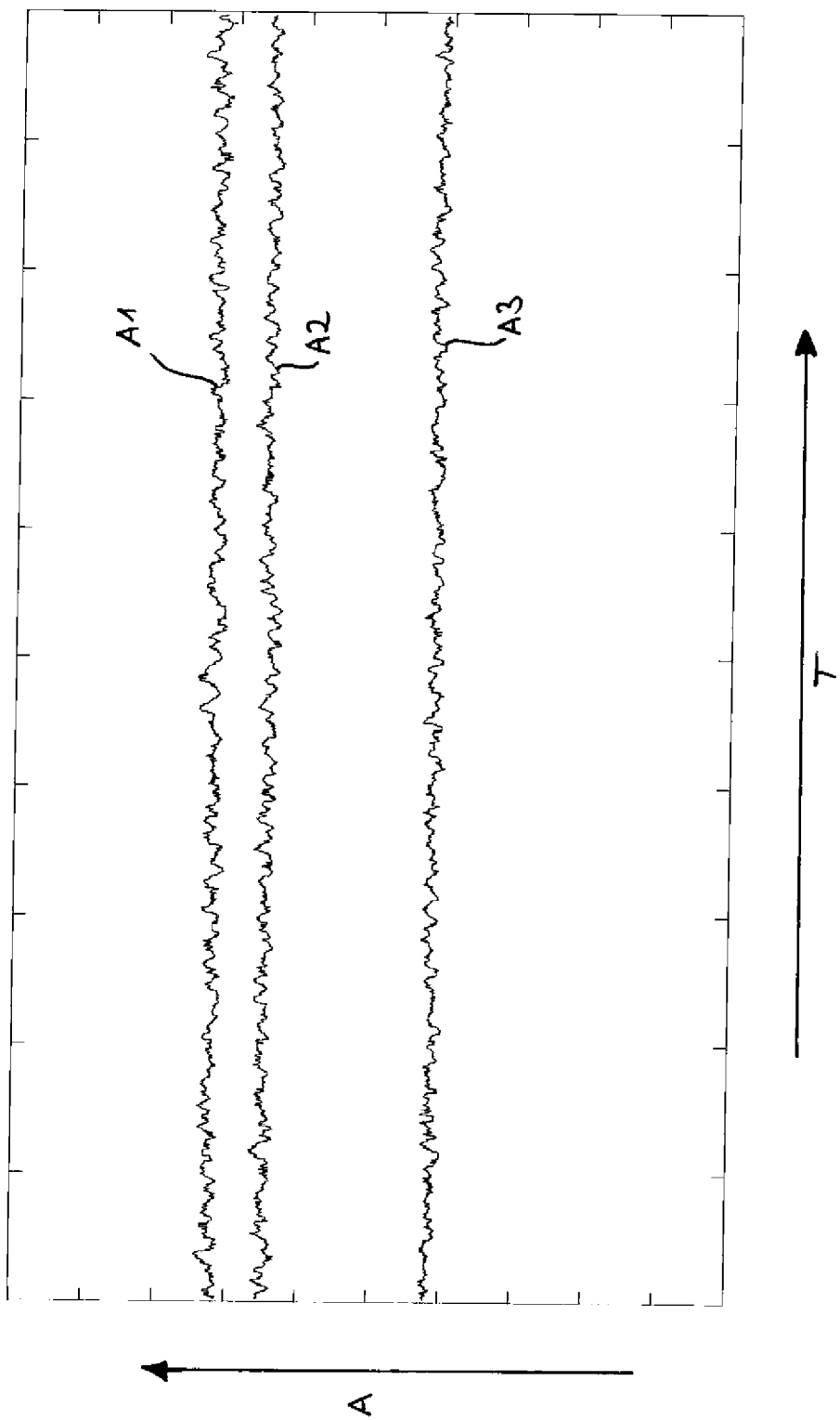

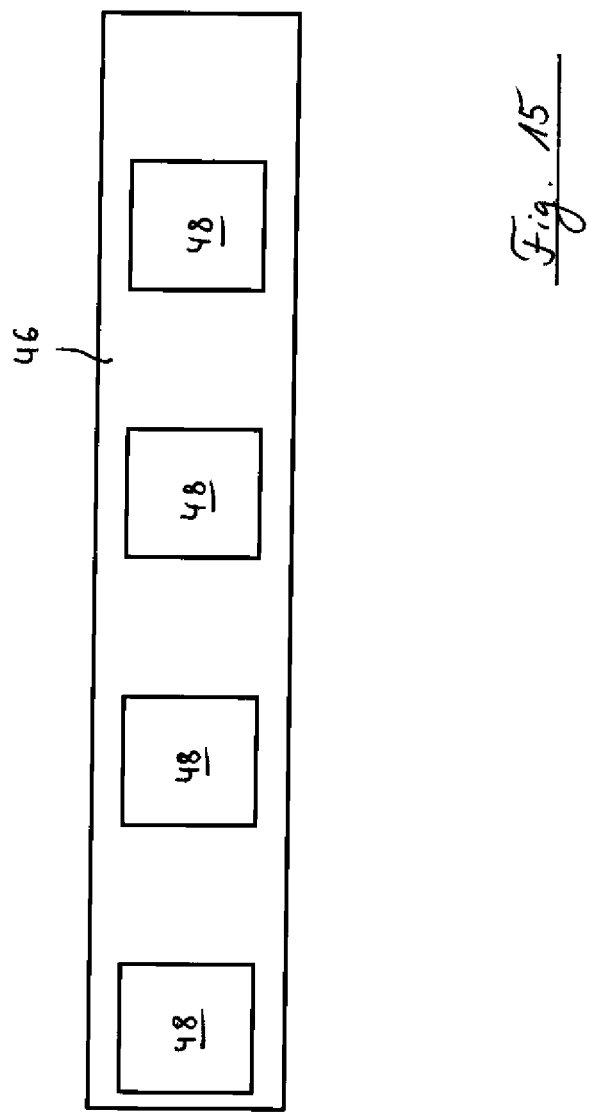

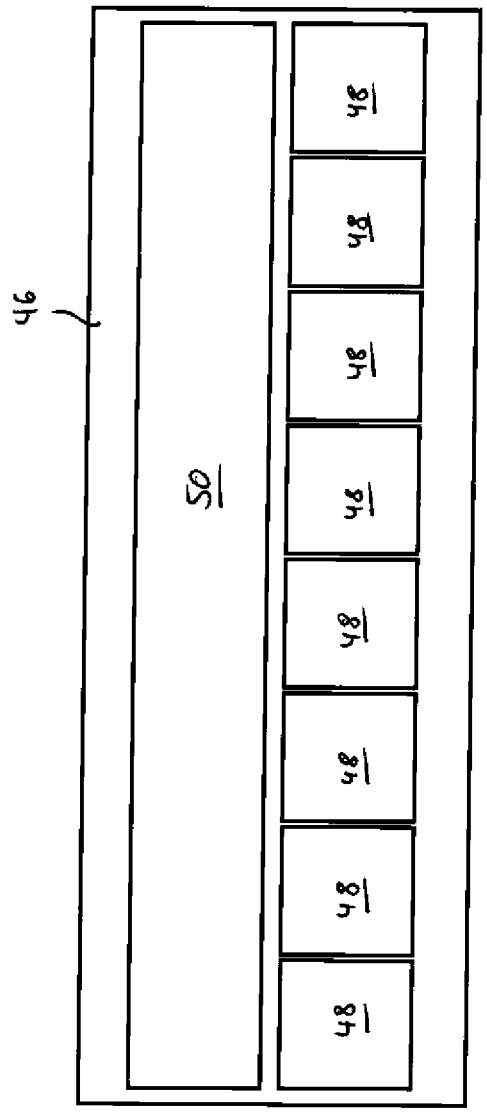

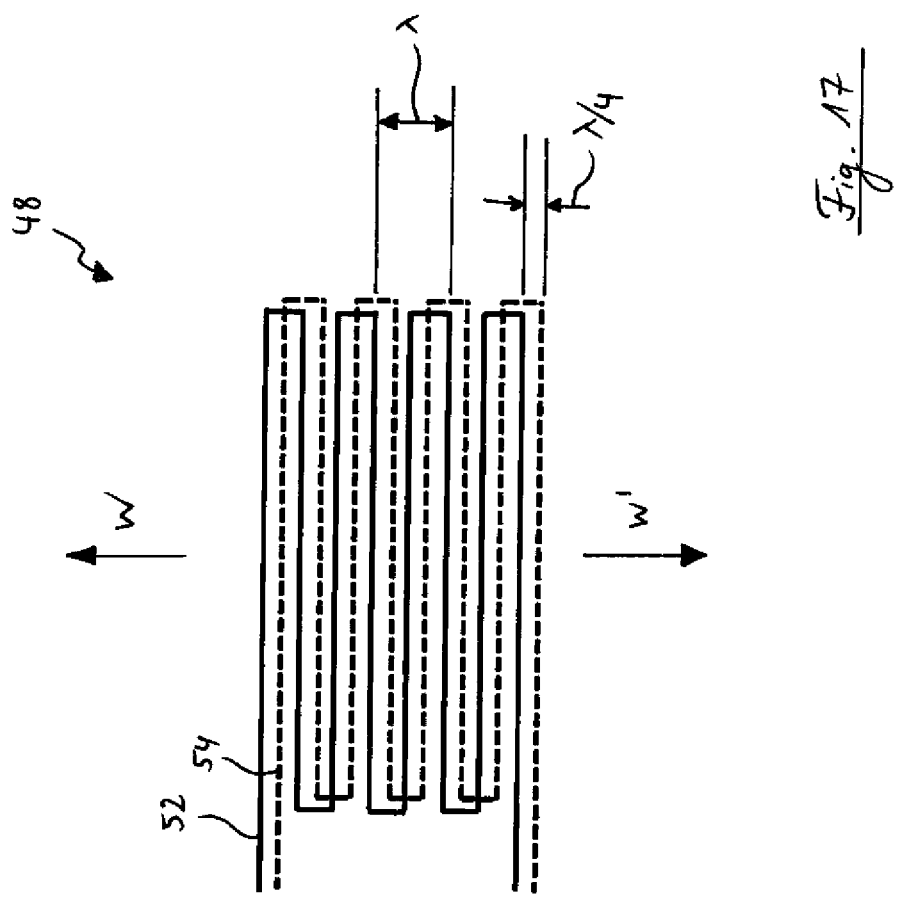

METHOD AND DEVICE FOR NON-INVASIVELY DETERMINING PROPERTIES OF A MULTIPHASE FLOW

CROSS REFERENCE

This application claims priority to PCT Application No. PCT/EP2019/077533, filed Oct. 10, 2019, which itself claims priority to German Patent Application No. 10 2018 125923.9, filed Oct. 18, 2018, the entirety of both of which are hereby incorporated by reference.

FIELD OF THE INVENTION

The invention relates to a method and a device for non-invasively determining properties of a multiphase flow which comprises a liquid fraction, in particular comprising water and/or a hydrocarbon-containing liquid, and a gaseous fraction and flows through an electrically conductive object, preferably a pipe or a pipeline.

BACKGROUND

The monitoring of media occurring as a mixture of different phases is relevant in the field of the oil and gas industry, for example, where inter alia oil-water-gas mixtures are conveyed or transported. The flow rates of the individual phases are of particular interest here, on the basis of which statements can be made for example about the conveyed quantity of oil. Non-invasive methods are distinguished here by the fact that the corresponding measuring devices or parts thereof are arranged externally on the pipes or pipelines and thus do not adversely affect the media transport.

Reliably determining properties of a multiphase flow constitutes a technical challenge. In particular, different measurement methods and/or measuring instruments may be particularly suitable for determining properties of individual fractions or phases of the multiphase flow. In practice, the use of a plurality of individual measuring instruments is laborious, however. The latter have to be positioned for example one behind another on the object, as a result of which a large amount of structural space is required. Moreover, the installation and maintenance of a plurality of measuring instruments is time-consuming and costly.

A further aspect to be considered when determining properties of a multiphase flow is that different kinds of flows may occur, in which the gaseous fraction and the liquid fraction may additionally have different flow rates. In the case of so-called stratified flow, the individual phases flow in layers lying one above another. However, this constitutes a rather rare special case for most applications. Particularly when conveying crude oil, so-called slug flow is the most frequently occurring type of flow. In this case, the gaseous fraction is predominantly transported in large bubbles—so-called Taylor bubbles—between which move slugs of the liquid fraction that fill the object diameter. Furthermore, there exists a range of types of flow that can be classified between stratified flow and slug flow. Furthermore, in the case of so-called annular flow, the liquid fraction flows annularly along the inner object wall, while the gaseous fraction flows centrally and in a manner spaced apart from the object wall by the liquid fraction.

BRIEF SUMMARY OF THE INVENTION

It is an object of the present invention to provide an improved method and an improved device for determining properties of a multiphase flow which yield reliable results in particular even when slug flow is present.

In the method according to the invention for non-invasively determining properties of a multiphase flow which flows through an electrically conductive object, preferably a pipe or a pipeline, using a single set-up having a plurality of EMAT transducers at least one property of the multiphase flow is determined by means of at least one measurement method. In particular, at least one of the following properties is determined:

the velocity of the gaseous fraction,
the velocity of the liquid fraction,
the flow cross-section fraction of the gaseous fraction and/or
the water content in the liquid fraction, wherein the flow cross-section fraction of the liquid fraction can also be determined instead of the flow cross-section fraction of the gaseous fraction.

In this case, at least one of the following measurement methods a) to e) is carried out:

a. at least two signals are spatially correlated with one another, in particular for determining the velocity of the gaseous fraction,
b. at least one signal arising on the basis of a wave (28) reflected from a reflection source (22) in the multiphase flow is evaluated, in particular for determining the velocity of the liquid fraction,
c. at least one signal arising on the basis of a wave (27) transmitted upstream and coupled at least into a part of the multiphase flow and at least one signal arising on the basis of a wave (27) transmitted downstream and coupled at least into a part of the multiphase flow are evaluated, in particular for determining the velocity of the liquid fraction,
d. at least one signal arising on the basis of a wave (27) transmitted downstream or upstream and coupled at least into a part of the multiphase flow is evaluated, in particular for determining the flow cross-section fraction of the gaseous fraction and/or for determining the water content in the liquid fraction (6),
e. at least one signal arising on the basis of a part of a wave (26) transmitted downstream or upstream, said part propagating exclusively in the object wall (4), is evaluated, in particular for determining the flow cross-section fraction of the gaseous fraction and/or for determining the water content in the liquid fraction (6).

By means of a skillful selection of one or preferably a plurality of measurement methods, from a group of relevant properties of the multiphase flow at least one of said properties is reliably determined according to the invention by means of a relatively small number of EMAT transducers. Furthermore, the invention provides for using a single EMAT set-up for all of the possible measurement methods, as a result of which the method is particularly practical. Only little space is required and no time is required for converting the set-up for the application of further measurement methods. The use of EMAT transducers makes it possible to dispense with a complex acoustic coupling by means of in particular gel-like coupling media. Moreover, particularly in connection with the generation of Lamb waves, higher tolerances are afforded in the positioning of the EMAT transducers with respect to one another, which increases the process reliability of a method employing different measurement methods in which one transducer cooperates possibly with a plurality of transducers at different positions. In particular, the method according to the invention is suitable for reliably determining properties of the multiphase flow even when a slug flow is present.

An EMAT transducer arranged at or near the object wall generates ultrasonic waves embodied in particular as guided waves, preferably as Lamb waves, in the magnetized or magnetic object wall. The waves propagate upstream and/or downstream in the object wall axially or parallel to a longitudinal central axis of the object. A portion of the ultrasonic waves couples at an oblique angle as a longitudinal wave into at least one part, for example the liquid or gaseous fraction or a single phase, of the multiphase flow. The angle at which the longitudinal wave couples in is determined by the phase velocity of the ultrasonic wave and the sound velocity of the part of the multiphase flow into which the longitudinal wave couples (angle relationship). In this case, the main propagation direction of the longitudinal wave always has a component in the downstream or upstream direction. The longitudinal waves coupled into the multiphase flow, for instance after they have crossed the flow or been reflected from a reflection source in the flow, can couple into the object wall in turn as ultrasonic waves embodied in particular as Lamb waves, this presupposing an entrance angle of the longitudinal wave corresponding to the angle relationship. Reflection sources are, in particular, phase boundaries in the multiphase flow, for example gas bubbles and/or gas voids in the liquid fraction, drops of oil in the water or else possibly solids. The ultrasonic waves generated in the object wall or coupled in from the flow can be detected by the same or a further EMAT transducer. In this case, such an ultrasonic wave ultimately induces an alternating current in at least one conductor track of the receiving EMAT transducer by way of eddy currents in the magnetized or magnetic object wall, which results in an electrical (reception) signal. Hereinafter, where it is not absolutely necessary, for ultrasonic waves it is not specified whether longitudinal waves or, for instance, guided waves are involved. They are referred to jointly as "waves". Furthermore, a wave which "couples into the multiphase flow" is understood to mean a wave which couples into at least one part of the multiphase flow. The generation of a wave and the detection of at least one signal arising on the basis of this wave are also referred to hereinafter as "pulse". Preferably one or a plurality of permanent magnets are used for magnetizing the object wall. Alternatively or supplementarily, it is possible to use one or a plurality of electromagnets in the quasi-steady state in comparison with the high-frequency alternating fields of the transducers.

A "single set-up" should be understood to mean a stationary arrangement of transducers that are to be positioned or are positioned at or near the object wall, wherein, for carrying out different measurement methods, neither the arrangement as a whole nor individual components of the arrangement need be altered spatially. This makes possible an easily handleable determination of properties of the multiphase flow, wherein such a set-up requires little space owing to the use of the electromagnetic acoustic transducers (EMAT transducers) and the coils thereof, which are generally of short construction in the direction of the pipeline.

For improved illustration, hereinafter a description is given of exemplary embodiments of the invention on the basis of an object embodied as a round pipe extending horizontally. However, the invention is not restricted to such objects.

In particular, at least the flow rate of the liquid fraction and/or the flow rate of the gaseous fraction are/is ascertained from at least two properties of the multiphase flow. Thus, at least one of the flow rates can be reliably determined without problems using one and the same set-up on the basis of fewer measurement methods.

Preferably for determining the velocity of the gaseous fraction, at least two signals are spatially correlated with one another, for determining the velocity of the liquid fraction (6), at least one signal arising on the basis of a wave (28) reflected from a reflection source (22) in the multiphase flow is evaluated, and/or at least one signal arising on the basis of a wave (27) transmitted upstream and coupled at least into a part of the multiphase flow and at least one signal arising on the basis of a wave (27) transmitted downstream and coupled at least into a part of the multiphase flow are evaluated and for determining the flow cross-section fraction of the gaseous fraction, at least one signal arising on the basis of a wave (27) transmitted downstream or upstream and coupled at least into a part of the multiphase flow is evaluated, and/or at least one signal arising on the basis of a part of a wave (26) transmitted downstream or upstream, said part propagating exclusively in the object wall (4), is evaluated.

These three properties can be ascertained without any problems using one and the same set-up of EMAT transducers on the basis of fewer measurement methods. In particular, the flow rate of the gaseous fraction and the flow rate of the liquid fraction can be determined on the basis of these properties.

For determining the velocity of the liquid fraction, in accordance with one embodiment of the invention, at least one signal arising on the basis of a wave reflected from a reflection source in the multiphase flow will be evaluated. A first transducer arranged at or near the object wall on a first side of the object generates a wave that propagates axially in the object wall, wherein a part of the wave couples into the multiphase flow at a specific angle. If the wave coupled into the multiphase flow impinges on a reflection source in the multiphase flow, it is reflected. If the entrance angle of the wave satisfies the angle relationship described above, the reflected wave couples into the object wall, wherein a signal arising on the basis of this wave is received.

Information regarding the velocity of the reflection source can be obtained from the signal. In particular, small reflection sources in the liquid fraction of the multiphase flow, such as gas voids, for example, move concomitantly with the liquid fraction, such that the velocity of the liquid fraction can be ascertained from the velocity of such reflection sources.

Preferably, periodically and for a specific time period waves (wave pulses) are generated and the signals arising on the basis of reflected waves are evaluated. If the reflection source does not move, a temporal position or a propagation time of the signal remains constant. From a shift of the temporal position of a signal attributed to a specific reflection source, conclusions are drawn about the velocity of the reflection source. This involves in particular the velocity component perpendicular to the reflection surface of the reflection source. It is evident that the repetition frequency of the generation of waves—also called pulse frequency hereinafter—must be sufficiently high. With a constant pulse frequency, the shift of the temporal position of the signals is generally proportional to the velocity of the reflection source. Preferably, a signal analysis, in particular a cross-correlation, is carried out for ascertaining whether two signals originate from the same reflection source. This involves in particular a so-called "pulsed Doppler measurement".

Preferably, a signal arising on the basis of a wave reflected from a reflection surface extending perpendicular to the main flow direction of the multiphase flow is evaluated. Said signal is received in particular by a further transducer arranged at or near the object wall on an opposite side relative to the first side of the object. An axial velocity of the reflection source extending parallel to the longitudinal direction of the object is ascertained in particular on the basis of the relationship $$v_\| = \tfrac{1}{2}\Delta t f_{PRF} c_{ph}$$

wherein $v_\|$ is the axial velocity of the reflection source, $\Delta t$ is the temporal shift of the signal, $f_{PRF}$ is the pulse repetition frequency and $c_{ph}$ is the phase velocity of the wave in the medium.

Alternatively or additionally, preferably a signal arising on the basis of a wave reflected from a reflection surface extending parallel to the main flow direction of the multiphase flow is evaluated. This signal is received in particular by a transducer arranged at or near the object wall on the first side of the object. Preferably, the first transducer is likewise embodied as a reception transducer and receives said signal. In a further embodiment according to the invention, the signal is received by a further transducer spaced apart from the first transducer in particular in the longitudinal direction of the object. A radial velocity of the reflection source extending perpendicular to the longitudinal direction of the object is ascertained in particular on the basis of the relationship $$v_\perp = \tfrac{1}{2} \Delta t\, f_{PRF}\, c_{ph} - \frac{1}{\tan \alpha \left( \frac{1}{\sin^2 \alpha} - 1 \right)}$$

wherein $v_\perp$ is the radial velocity of the reflection source, $\Delta t$ is the temporal shift of the signal, $f_{PRF}$ is the pulse repetition frequency, $c_{ph}$ is the phase velocity of the wave in the medium and $a$ is the angle between the main propagation direction of the wave coupled into the multiphase flow and a perpendicular at right angles to the inner wall of the object.

Alternatively or additionally, preferably a signal arising on the basis of a wave reflected from a reflection surface extending perpendicular to the main propagation direction of the wave coupled into the multiphase flow is evaluated. Such a reflection surface has the effect that the wave coupled into the multiphase flow is reflected back by 180°. Said reflection surface usually extends neither parallel nor perpendicular to the longitudinal direction of the object. In this embodiment, the temporal shift of the signal in accordance with the formula $$v_\| + v_\perp \tan \alpha \left( \frac{1}{\sin^2 \alpha} - 1 \right) = \tfrac{1}{2} \Delta t\, f_{PRF}\, c_{ph}$$

is dependent both on the axial and on the radial velocity component of the reflection source, wherein $v_\perp$ is the radial velocity component of the reflection source, $v_\|$ is the axial velocity component of the reflection source, $\Delta t$ is the temporal shift of the signal, $f_{PRF}$ is the pulse repetition frequency, $c_{ph}$ is the phase velocity of the wave in the medium and $a$ is the angle between the main propagation direction of the wave coupled into the multiphase flow and a perpendicular at right angles to the inner wall of the object. This signal is received in particular by a transducer arranged at or near the object wall on the first side of the object. This can be the first transducer, provided that the latter is configured for receiving signals, or a further transducer spaced apart from the first transducer in particular in the longitudinal direction of the object.

In combination with the ascertained velocity of a reflection source that moves exclusively radially, the axial velocity component can be ascertained in isolation. Alternatively, in combination with the ascertained velocity of a reflection source that moves exclusively axially, the radial velocity component can be ascertained in isolation. For ascertaining both the radial and the axial velocity of reflection sources, it is therefore sufficient to observe two of the three types of reflection source described above.

Preferably, for ascertaining the velocity of the reflection sources, at least one, in particular transmitting, transducer is arranged at a bottommost position (6 o'clock position) of the object. This increases the probability of the waves coupling into the liquid fraction, since for most types of flow the majority of the gaseous fraction collects in an upper region of the object (10 o'clock position to 2 o'clock position), in particular in a topmost region of the object (12 o'clock position).

Advantageously, Lamb waves are generated by the transmitting transducer in the object wall. Said waves couple as so-called "leaky Lamb waves" into the medium via a wide longitudinal section of the object wall. As a result, the moving reflection sources can be observed over a greater path distance. Furthermore, more energy is made available for the longitudinal waves coupling into the medium.

As an alternative or in addition to ascertaining the velocity of the reflection source on the basis of the shift of the temporal position of the signal, in accordance with a further embodiment of the invention, a frequency shift of the signal arising on the basis of a wave reflected from a reflection source in the multiphase flow is evaluated. The Doppler effect makes it possible to draw conclusions about the velocity of the reflection source from the frequency shift. The velocity of the reflection source can thus be determined even more reliably. This involves in particular a so-called "continuous-wave Doppler measurement".

The above-described measurement method for determining the velocity of the liquid fraction of the multiphase flow on the basis of an evaluation of signals arising on the basis of a wave reflected from a reflection surface extending perpendicular or parallel to the main flow direction of the multiphase flow or perpendicular to the main propagation direction of the wave coupled into the multiphase flow can also be carried out as an independent method detached from the further measurement methods described.

In particular, this method is likewise carried out using the minimum set-up of transducers as described below. For carrying out different measurement methods, a realignment of the transducers is therefore not required, as a result of which a determination of properties of the multiphase flow is more practical.

For determining the velocity of the liquid fraction, in accordance with one embodiment of the invention, at least one signal arising on the basis of a wave transmitted upstream and coupled at least into a part of the multiphase flow and at least one signal arising on the basis of a wave transmitted downstream and coupled at least into a part of the multiphase flow are evaluated.

These waves coupled into at least one part of the multiphase flow cross the multiphase flow and couple into the object wall. In one embodiment according to the invention, the velocity of the liquid fraction is determined from the propagation time difference between the two signals. This involves in particular a so-called "propagation time difference measurement".

Preferably, the waves each have at least one propagation path extending between a 3 o'clock position and a 9 o'clock position. The propagation paths preferably extend in a plane extending at least substantially transversely with respect to the direction of gravitation. This increases the probability of the waves crossing the liquid fraction since, for most types of flow, the majority of the gaseous fraction collects in an upper region of the object (in particular 12 o'clock position). A plane extends substantially transversely with respect to the gravitational direction if its angle of intersection with the gravitational direction is 90°±10°.

Such a configuration is realized in particular by an arrangement of two transducers arranged upstream on opposite sides of the object and two transducers arranged downstream on opposite sides of the object.

In particular, for calculating the propagation times, in each case a signal arising on the basis of a part of the transmitted wave that propagates exclusively in the object wall (direct wall signal) is used as reference.

In particular, this method is likewise carried out using the minimum set-up of transducers as described below. For carrying out different measurement methods, a realignment of the transducers is therefore not required, as a result of which a determination of properties of the multiphase flow is more practical.

For determining the velocity of the gaseous fraction, at least two signals are spatially correlated with one another. Signals which are received in a manner offset in time at two different positions and which arise on the basis of waves interacting with a medium and have a common characteristic signal property, for example in the form of a specific signal pattern, can provide information about velocities in the medium. In particular, the velocities of individual phases or fractions of the multiphase flow can thus be ascertained.

Preferably, at least two signals at two positions spaced apart from one another in the longitudinal direction of the object are correlated with one another. In particular, signals attributed to waves that interact with reflection sources in the multiphase flow are evaluated in this case.

A first transducer arranged at or near the object wall on a first side of the object generates a wave that propagates axially in the object wall, wherein a part of the wave couples into the multiphase flow at a specific angle. If the wave coupled into the multiphase flow impinges on a reflection source in the multiphase flow, it is reflected. I the entrance angle of the wave satisfies the angle relationship mentioned above, it couples into the object wall.

Preferably, the signal arising on the basis of the reflected wave is analysed with regard to at least one signal property, for example an amplitude fluctuation. If this signal characteristic is observed at two positions spaced apart from one another in the longitudinal direction of the object, the velocity of the associated reflection source can be determined on the basis of the time that has elapsed between the two observations and also the distance between the two positions.

This measurement method is realized in particular by two transducers arranged on the same side of the object and spaced apart from one another in the longitudinal direction of the object. In this case, preferably each transducer is configured for transmission and reception, such that the generated wave and the signal arising on the basis of the reflected wave are transmitted and received, respectively, by the same transducer.

Alternatively, in accordance with a further embodiment of the invention, this measurement method is realized by two transducer pairs arranged in a manner spaced apart from one another in the longitudinal direction of the object and each having at least one transmission transducer and a reception transducer. Preferably, transmission transducer and reception transducer here are arranged opposite one another in relation to a longitudinal central axis of the object.

In particular, the maximum distance between the correlation positions amounts to ten times the pipe diameter, preferably four times the pipe diameter.

Preferably, various signal properties, such as frequency, amplitude and/or phase, are used for the correlation of two signals. In particular, a frequency shift of the signal arising on the basis of a wave reflected from a reflection source in the multiphase flow is evaluated. Preferably, the correlation comprises a cross-correlation.

In particular, this method is likewise carried out using the minimum set-up of transducers as described below. For carrying out different measurement methods, a realignment of the transducers is therefore not required, as a result of which a determination of properties of the multiphase flow is more practical.

For determining the flow cross-section fraction of the gaseous fraction (gas void fraction), in accordance with one embodiment of the invention, at least one signal arising on the basis of a wave transmitted downstream or upstream and coupled at least into a part of the multiphase flow is evaluated.

Depending on the flow cross-section fraction of the gaseous fraction, the wave coupled into the multiphase flow either is reflected in particular at a reflection surface extending parallel to the main flow direction of the multiphase flow or crosses the multiphase flow at least once or is transmitted at least once through the multiphase flow.

For the case where the multiphase flow has a sufficiently large, continuous gaseous fraction (not exclusively small gas voids) along the propagation path of the wave, this fraction will generally collect in an upper region, in particular in proximity to the 12 o'clock position. The phase boundary between the upper gaseous fraction and the liquid fraction will at least partly form a quantity of reflection sources having a horizontally extending reflection surface. Preferably, the flow cross-section fraction of the gaseous fraction is then determined by way of a measurement of the height of the phase boundary. The height of the phase boundary is calculated in particular from the propagation time of a signal arising on the basis of the wave reflected at a horizontally extending reflection surface. Preferably, larger gas bubbles in the multiphase flow, in particular Taylor bubbles when slug flow is present, are thus detected. In particular, for calculating the propagation time, a signal arising on the basis of a part of the transmitted wave that propagates exclusively in the object wall (direct wall signal) is used as reference.

For the case where the multiphase flow consists substantially (at least apart from small gas voids) of liquid fraction along at least one propagation path of the wave, the wave can cross the multiphase flow and couple into the object wall. The signal arising on the basis of the wave crossing the multiphase flow is preferably evaluated. This signal is an indicator that the flow cross-section at least along a propagation path of the wave is completely occupied by liquid fraction of the multiphase flow.

For the case where the multiphase flow consists (at least apart from small gas voids) of liquid fraction along a larger longitudinal section of the object, the wave coupled into the multiphase flow from a first side of the object wall can cross the multiphase flow twice, wherein the wave is reflected on the opposite side and couples into the object wall on the first side thereof. The signal arising on the basis of the wave crossing the multiphase flow at least twice is preferably evaluated. This signal is an additional indicator that the flow cross-section at least along a propagation path of the wave is completely occupied by liquid fraction of the multiphase flow, the evaluation of which enables the flow cross-section fraction of the gaseous fraction to be determined more accurately.

In particular, in this case, at least one transmitting transducer is arranged at the 6 o'clock position. Preferably, at least one receiving transducer is arranged at the 6 o'clock position. In particular, at least one receiving transducer is arranged at the 12 o'clock position. As a result, a propagation path extending between the 6 o'clock position and the 12 o'clock position is provided for the wave, such that the flow cross-section fraction of the gaseous fraction can be optimally determined.

The above-described measurement method for determining the flow cross-section fraction of the gaseous fraction of the multiphase flow on the basis of an evaluation of signals arising on the basis of a wave reflected from a reflection source in the multiphase flow or a wave transmitted at least once through at least one part of the multiphase flow can also be carried out as an independent method detached from the further measurement methods described.

In particular, this method is likewise carried out using the minimum set-up of transducers as described below. For carrying out different measurement methods, a realignment of the transducers is therefore not required, as a result of which a determination of properties of the multiphase flow is more practical.

For determining the flow cross-section fraction of the gaseous fraction (gas void fraction), in accordance with a further embodiment of the invention, at least one signal arising on the basis of a part of a wave transmitted downstream or upstream, said part propagating exclusively in the object wall, is evaluated.

A wave generated in the object wall couples into the multiphase flow with different degrees of success depending on the composition of that part of the multiphase flow which adjoins the object wall, in particular depending on the sound velocity and/or density in said part. Conclusions about the composition of that part of the multiphase flow which adjoins the object wall can thus be drawn in particular from the attenuation of the amplitude.

The composition of the multiphase flow comprises in particular the information as to whether a liquid or gaseous fraction is involved. Furthermore, the composition also comprises information about whether the liquid fraction is water or a hydrocarbon-containing liquid. That part of the multiphase flow which adjoins the object wall can be the liquid fraction, for example, to which, as oil-water mixture having a specific water fraction, a sound velocity of the mixture is assigned.

Preferably, the at least one signal arising on the basis of a part of a wave transmitted upstream or downstream at a first position, said part propagating exclusively in the object wall, is received at a second position spaced apart from the first position in the longitudinal direction of the object, wherein the composition of that part of the multiphase flow which adjoins the object wall is ascertained on the basis of the amplitude of the signal.

Conclusions about the flow cross-section fraction of the gaseous and/or the liquid fraction are obtained by ascertaining the composition of the multiphase flow at a plurality of circumferential positions of the object.

Preferably, a plurality of propagation paths extending parallel to the longitudinal direction of the object are provided along the circumference of the object. In particular, a wave—preferably generated by a transducer encompassing the object circumferentially at a first position or along a first object cross-section—is transmitted upstream or downstream fully circumferentially into the object wall, wherein the signals arising on the basis of that part of said wave which propagates exclusively in the object wall, at a second object cross-section spaced apart from the first object cross-section in the longitudinal direction of the object or at a second position, are received at at least two different circumferential positions. In this case, the received signals are attributed to a common wave or possibly to a common wave pulse or wave burst and can therefore be better compared with one another. Alternatively, in accordance with a further embodiment of the invention, a plurality of individually generated waves are transmitted along the circumference of the object.

Preferably, at the second position or along the second object circumference, signals are received at at least four, preferably at least six, particularly preferably at least eight, a maximum of 40, different circumferential positions. The flow cross-section fraction of the gaseous fraction can be determined more reliably therefrom.

For improved determination of the composition of the multiphase flow, the extent of the attenuation of the amplitude is preferably calibrated on the basis of known compositions.

The above-described measurement method for determining the flow cross-section fraction of the gaseous fraction of the multiphase flow on the basis of an evaluation of signals arising on the basis of parts of waves transmitted downstream or upstream, said parts propagating exclusively in the object wall, can also be carried out as an independent method detached from the further measurement methods described.

In particular, this method is likewise carried out using the minimum set-up of transducers as described below. For carrying out different measurement methods, a realignment of the transducers is therefore not required, as a result of which a determination of properties of the multiphase flow is more practical.

In accordance with a further embodiment of the invention, for determining the water content in the liquid fraction (so-called water liquid ratio, WLR), at least one signal arising on the basis of a part of a wave transmitted downstream or upstream, said part propagating exclusively in the object wall, is evaluated for determining the water content in the liquid fraction.

A wave generated in the object wall couples into the multiphase flow with different degrees of success depending on the composition of that part of the multiphase flow which adjoins the object wall, in particular depending on the sound velocity in said part. Conclusions about the composition, in particular the water content in the liquid fraction of the multiphase flow, of that part of the multiphase flow which adjoins the object wall can thus be drawn in particular from the attenuation of the amplitude.

Preferably, transmission transducers and reception transducers are arranged in a lower circumferential region extending between the 3 o'clock position and the 9 o'clock position, preferably between the 4 o'clock position and the 8 o'clock position. This ensures for most applications that the transducers are arranged at those regions of the object wall behind which the liquid fraction of the multiphase flow is situated. In particular, in this case, at least one transmitting transducer is arranged at the 6 o'clock position. Preferably, at least one receiving transducer is arranged at the 6 o'clock position.

The above-described measurement method for determining the water content in the liquid fraction of the multiphase flow on the basis of an evaluation of at least one signal arising on the basis of part of at least one wave transmitted downstream or upstream, said part propagating exclusively in the object wall, can also be carried out as an independent method detached from the further measurement methods described.

In particular, this method is likewise carried out using the minimum set-up of transducers as described below. For carrying out different measurement methods, a realignment of the transducers is therefore not required, as a result of which a determination of properties of the multiphase flow is more practical.

In accordance with a further embodiment of the invention, for determining the water content in the liquid fraction, at least one signal arising on the basis of a wave transmitted upstream or downstream and coupled at least into a part of the multiphase flow is evaluated. Preferably, a signal arising on the basis of the wave crossing the multiphase flow, in particular the liquid fraction thereof, is evaluated.

In one embodiment according to the invention, the sound velocity of the liquid fraction is ascertained from the propagation time of a signal arising on the basis of a wave crossing the liquid fraction. With knowledge of the sound velocity of the individual components of the liquid fraction, i.e. of the water and/or of the hydrocarbon-containing liquid, the respective fraction of the component and thus the water content in the liquid fraction can be ascertained.

In particular, for calculating the propagation time, a signal arising on the basis of a part of the transmitted wave that propagates exclusively in the object wall (direct wall signal) is used as reference.

Preferably, the waves each have at least one propagation path extending between a 3 o'clock position and a 9 o'clock position. The propagation paths extend in particular in a plane extending substantially transversely with respect to the direction of gravitation. This increases the probability of the waves crossing the liquid fraction since, for most types of flow, the majority of the gaseous fraction collects in an upper region of the object (10 o'clock position to 2 o'clock position), in particular in a topmost position (12 o'clock position).

Such a configuration is realized in particular by an arrangement of two transducers spaced apart in the longitudinal direction of the object on two opposite sides of the object. Preferably, a further reception transducer is arranged on the same side on which the transmission transducer is arranged, in order to receive a direct wall signal.

Preferably, the water content in the liquid fraction is determined firstly by means of a wave transmitted downstream and secondly by means of a wave transmitted upstream. Accordingly, for determining the water content in the liquid fraction, at least one signal arising on the basis of a wave transmitted upstream or downstream and coupled at least into a part of the multiphase flow and a signal arising on the basis of a further wave transmitted in the respective other direction (upstream or downstream) and coupled at least into a part of the multiphase flow are evaluated. From the combination of the two results, the water content in the liquid fraction can be determined more accurately. Such a configuration is realized in particular by an arrangement of two transducers arranged upstream on opposite sides of the object and two transducers arranged downstream on opposite sides of the object. In particular, this method is likewise carried out using the minimum set-up of transducers as described below. For carrying out different measurement methods, a realignment of the transducers is therefore not required, as a result of which a determination of properties of the multiphase flow is more practical.

In one preferred embodiment of the invention, at least one of the measurement methods is assigned configuration parameters on the basis of which the transducers necessary for the measurement method are controlled. The configuration parameters are taken as a basis for determining, in particular, which transducers transmit at which point in time, with which pulse repetition frequency, in a pulse- or burst-like manner, with which frequency and/or with which amplitude. As a result, different measurement methods can be efficiently carried out in parallel or sequentially. Furthermore, the configuration parameters are taken as a basis for determining, in particular, which transducers receive in which time intervals, wherein reception preferably begins only after a predefined delay time has elapsed after the signal to be received has been transmitted. As a result, particularly when different measurement methods are carried out in parallel, more targeted reception of signals can be ensured.

In accordance with a further preferred configuration of the invention, at least one of the transducers is used both as transmitter and as receiver. As a result, the number of transducers required for carrying out the method can be reduced, as a result of which the method is more practical. Preferably, all the transducers are embodied in such a way that they are usable both as transmitter and as receiver.

In a further preferred embodiment of the invention, one of the transducers transmits directionally upstream and/or downstream. The emission of waves is thus effected purposefully according to the respective necessity of the measurement method. In this regard, waves can be transmitted for example predominantly in the direction of a receiver. By contrast, no or hardly any waves are transmitted along other propagation paths, as a result of which a better signal-to-noise ratio is also achieved. For this purpose, the transmitting EMAT transducer is preferably embodied as a phased array transducer. Preferably, all the transducers are embodied as phased array transducers.

In accordance with a further preferred configuration of the invention, at least one of the transducers generates Lamb waves in the object wall. Lamb waves couple into the medium as so-called "leaky Lamb waves" over a wide longitudinal section of the object wall and can therefore interact with said medium over the entire longitudinal section. In particular, moving reflection sources in the multiphase flow can be better detected in this way.

In a further preferred embodiment of the invention, for at least one property of the multiphase flow the measurement method determining it is selected depending on the ratio of gaseous fraction to liquid fraction of the multiphase flow. Preferably, for at least one property of the multiphase flow the measurement method determining it is selected depending on the flow rate of the liquid fraction and/or the flow rate of the gaseous fraction.

As the content of gaseous fraction increases, the ability of waves to cross the multiphase flow is poorer, and so measurement methods based thereon function only to a limited extent. Preferably, therefore, for determining the velocity of the liquid fraction and/or for determining the water content in the liquid fraction with an increasing content of gaseous fraction, measurement methods based on a transmission of the waves through the multiphase flow are dispensed with and a further measurement method is used instead. In particular, alternatively, the further measurement method for determining the respective property is carried out additionally and the results of the measurement method based on a transmission of the waves and of the further measurement method are evaluated jointly. This applies particularly in the case of a GVF value of greater than or equal to 50%.

As the content of gaseous fraction decreases, the number of reflection sources in the multiphase flow also decreases, and so measurement methods in which signals produced on the basis of waves reflected at reflection sources are evaluated function only to a limited extent. Preferably, therefore, for determining the velocity of the liquid fraction and/or for determining the flow cross-section fraction of the gaseous fraction with a decreasing content of gaseous fraction, measurement methods in which signals produced on the basis of waves reflected at reflection sources are evaluated are dispensed with and a further measurement method is used instead. In particular, alternatively, the further measurement method for determining the respective property is carried out additionally and the results of the measurement method based on a transmission of the waves and of the further measurement method are evaluated jointly. This applies particularly in the case of a GVF value of less than 50%.

The use of two different, in particular mutually complementary, methods ensures a reliable determination of the respective property under different conditions. In particular, the use of the set-up described below makes it possible, without any problems, to choose between different, in particular mutually complementary, measurement methods, without realigning individual transducers or the entire set-up.

In accordance with a further preferred configuration of the invention, for determining at least one of the properties for at least one measurement method a plurality of individual measurements are carried out and evaluated, wherein in particular a mean value and/or a maximum are/is ascertained. In this regard, in particular, fluctuating measurement values can be recorded over a longer period of time and properties of the multiphase flow can be determined reliably. Particularly when slug flow is present, properties such as, for example, the velocity of the liquid fraction or the flow cross-section of the gaseous fraction are subject to relatively strong fluctuations, and so they are preferably determined at least over a plurality of slug passes on the basis of a plurality of individual measurements and the results are then used for forming a mean value (over time).

In a further preferred embodiment of the invention, for at least one measurement method a pulse repetition frequency of at least 200 Hz, preferably at least 400 Hz, particularly preferably at least 800 Hz, and a maximum of 5 kHz, is used. Thus, in particular, greatly fluctuating properties of the multiphase flow are determined with sufficient time resolution, and so a reliable mean value can be formed in this way. Furthermore, by means of different measurement methods carried out in parallel or sequentially, it is possible to determine a plurality of properties which, on account of their being ascertained in temporal proximity, can be factored into calculations together or be related to one another in some other way. The respective pulse repetition frequency for the respective measurement method depends, in particular, on the fluctuation of individual or a plurality of properties. Preferably, such a pulse repetition frequency is used if, for determining the velocity of the liquid fraction, at least one signal arising on the basis of a wave reflected from a reflection source in the multiphase flow is evaluated. In particular, a pulse repetition frequency of 1 Hz to 50 Hz, preferably of 5 Hz to 25 Hz, is used in other measurement methods.

In particular, in the evaluation of temporal positions of signals, for example for ascertaining propagation time differences, a signal arising on the basis of a part of a wave transmitted downstream or upstream, said part propagating exclusively in the object wall, is used as reference signal.

The flow rate $Q_L$ of the liquid fraction is ascertained in particular on the basis of the following formula $$Q_L = A\overline{v_L}(1-\overline{\varepsilon_G}),$$

wherein A is the cross-sectional area of the object, $\overline{v_L}$ is the averaged velocity of the liquid fraction, and $\overline{\varepsilon_G}$ is the averaged flow cross-section fraction of the gaseous fraction.

The flow rate $Q_G$ of the gaseous fraction is ascertained in particular on the basis of the following formula $$Q_G = A\overline{v_G}\overline{\varepsilon_G},$$

wherein A is the cross-sectional area of the object, $\overline{v_G}$ is the averaged velocity of the gaseous fraction, and $\varepsilon_G$ is the averaged flow cross-section fraction of the gaseous fraction.

The total flow rate $Q_T$ is thus ascertained in particular by means of the following relation:

$$Q_T = Q_F + Q_G$$

The proportion of the total flow rate which is made up of the flow rate of the gaseous fraction (so-called gas volume fraction, GVF) is ascertained in particular as follows:

$$GVF = \frac{Q_G}{Q_F + Q_G} = \frac{Q_G}{Q_T}$$

In accordance with the description already given above and that which will be given further below, the object stated in the introduction is also achieved by means of a device for non-invasively determining properties of a multiphase flow which comprises a liquid fraction, in particular comprising water and/or a hydrocarbon-containing liquid, and a gaseous fraction and flows through an electrically conductive object, preferably a pipe or a pipeline. The device comprises at least four EMAT transducers to be positioned upstream along a first object cross-section at or near the object wall and at least four EMAT transducers to be positioned downstream along a second object cross-section at or near the object wall. Respectively two of the transducers to be positioned upstream and respectively two of the transducers to be positioned downstream are arranged opposite one another, in particular diametrically opposite one another in the case of a tubular object, on the object. The positions of the transducers to be positioned upstream are varied relative to the positions of the transducers to be positioned downstream only in the longitudinal direction of the object. Furthermore, the device comprises a control unit, which, in particular on the basis of specific configuration parameters, controls the transducers necessary for the respective measurement method, and an evaluation unit, which evaluates the data generated from the received signals.

Control unit and evaluation unit are preferably combined in a common unit. In particular, control unit and evaluation unit are alternatively positioned at different locations.

With a device of this type, a plurality of properties of the multiphase flow can be reliably determined with a relatively small number of EMAT transducers. By virtue of the simple set-up of EMAT transducers, the device can be produced, installed and maintained with little expenditure in terms of time and costs.

By virtue of the use of EMAT transducers, it is possible to dispense with a complex acoustic coupling by means of in particular gel-like coupling media. Moreover, higher tolerances are afforded in the positioning of the EMAT transducers with respect to one another, which simplifies the production and installation of the device.

In one preferred embodiment of the invention, EMAT transducers arranged along one of the object cross-sections in their entirety at least substantially cover the object in a circumferential direction. The object is deemed to be substantially covered if at least 90% of the circumference is covered by the transducers. The object is deemed to be completely covered in particular even if there are technically governed minimum distances between the individual transducers in the circumferential direction of the object.

In accordance with a further preferred configuration of the invention, the device comprises along a first object cross-section and/or a second object cross-section in each case at least six, preferably at least eight, in particular a maximum of 40, EMAT transducers to be positioned at or near the object wall. In particular for determining the flow cross-section fraction of the gaseous fraction of the multiphase flow on the basis of an evaluation of signals arising on the basis of parts of waves transmitted downstream or upstream, said parts propagating exclusively in the object wall, a better resolution along the circumference of the object is thus achieved, as a result of which this property can be determined more reliably. The number of transducers used is dependent, in particular, on the object or pipe diameter, a higher number of transducers tending to be provided for larger diameters.

In a further preferred embodiment of the invention, the device furthermore comprises at least one EMAT transducer encompassing the object substantially fully circumferentially. Such a transducer can transmit a wave upstream or downstream fully circumferentially into the object wall, which is advantageous in particular for determining the flow cross-section fraction of the gaseous fraction of the multiphase flow. In this case, signals arising on the basis of that part of said wave which propagates exclusively in the object wall are received at at least two different circumferential positions. These signals are attributed to a common wave or possibly to a common wave pulse or wave burst and can therefore be better compared with one another. The object is deemed to be substantially covered if at least 90%, preferably at least 95%, of the circumference is covered by the EMAT transducer.

In accordance with a further preferred configuration of the invention, the device comprises at least two EMAT transducers embodied fully circumferentially, wherein a first EMAT transducer embodied fully circumferentially is arranged upstream of the at least four EMAT transducers to be positioned upstream along a first object cross-section at or near the object wall, and a second EMAT transducer embodied fully circumferentially is arranged downstream of the at least four EMAT transducers to be positioned downstream along a second object cross-section at or near the object wall. This symmetrical arrangement makes it possible to carry out at least the majority of the measurement methods described above independently of the main flow direction of the multiphase flow.

In a further preferred embodiment of the invention, at least one of the transducers is embodied as a phased array transducer comprising at least two coils which are spatially offset with respect to one another. As a result of the spatial offset in combination with a corresponding phase offset of the excitation currents, a wave can thereby be transmitted directionally upstream or downstream in the object wall. The emission of waves is thus effected purposefully and in particular according to the respective necessity of the measurement method. In this regard, waves can be transmitted for example predominantly in the direction of a receiver. By contrast, no or hardly any waves are transmitted along other propagation paths, as a result of which a better signal-to-noise ratio is also achieved.

In accordance with a further preferred configuration of the invention, in a radial direction of the object above at least one first transducer configured for generating ultrasonic waves having a first wavelength, there is arranged at least one further transducer configured for generating ultrasonic waves having a different wavelength. This makes it possible, depending on the application, to select a wavelength that is optimal for determining at least one property. In this case, preferably, transducers having a longer wavelength are arranged above transducers having a shorter wavelength.

In a further preferred embodiment of the invention, the device has at least one flexible carrier, in which are arranged the transducers to be positioned upstream and/or the transducers to be positioned downstream and/or the EMAT transducers embodied fully circumferentially. As a result, the transducers and in particular their coils can be positioned optimally at the outer contour of the object wall. Moreover, a positioning of the transducers with respect to one another (for example 12 o'clock, 3 o'clock, 6 o'clock and 9 o'clock positions of the transducers that are not embodied fully circumferentially) can be predefined depending on the pipe diameter, which makes the installation of the device more practical. Furthermore, this enables the cost-effective production of a plurality of transducers having different wavelengths that are arranged one above another. Preferably, the coils of the transducers are printed on a flexible printed circuit board, in particular in the copper pattern.

In a further preferred embodiment of the invention, the coils of a transducer are arranged one above another in a radial direction of the longitudinal central axis of the object, in particular in different layers of the carrier. This enables particularly simple production of transducers embodied in particular as phased array transducers having coils offset with respect to one another.

BRIEF DESCRIPTION OF THE DRAWINGS

Reference is now made more particularly to the drawings, which illustrate the best presently known mode of carrying out the invention and wherein similar reference characters indicate the same parts throughout the views.

FIG. 11 shows a further embodiment of the invention.

FIG. 12 shows a diagram with measurement results in accordance with the embodiment from FIG. 11

FIG. 14 shows a diagram with measurement results in accordance with the embodiment from FIG. 13.

FIG. 15 shows a further embodiment of the invention.

FIG. 16 shows a further embodiment of the invention.

FIG. 17 shows a detail of a transducer in a further embodiment of the invention.

DETAILED DESCRIPTION OF THE DRAWINGS

Identically or similarly acting parts are provided—in so far as expedient—with identical reference signs. Individual technical features of the exemplary embodiments described below can also lead to developments according to the invention together with the features of the exemplary embodiments described above, but at least together with the features of one of the independent claims.

Figure 1:
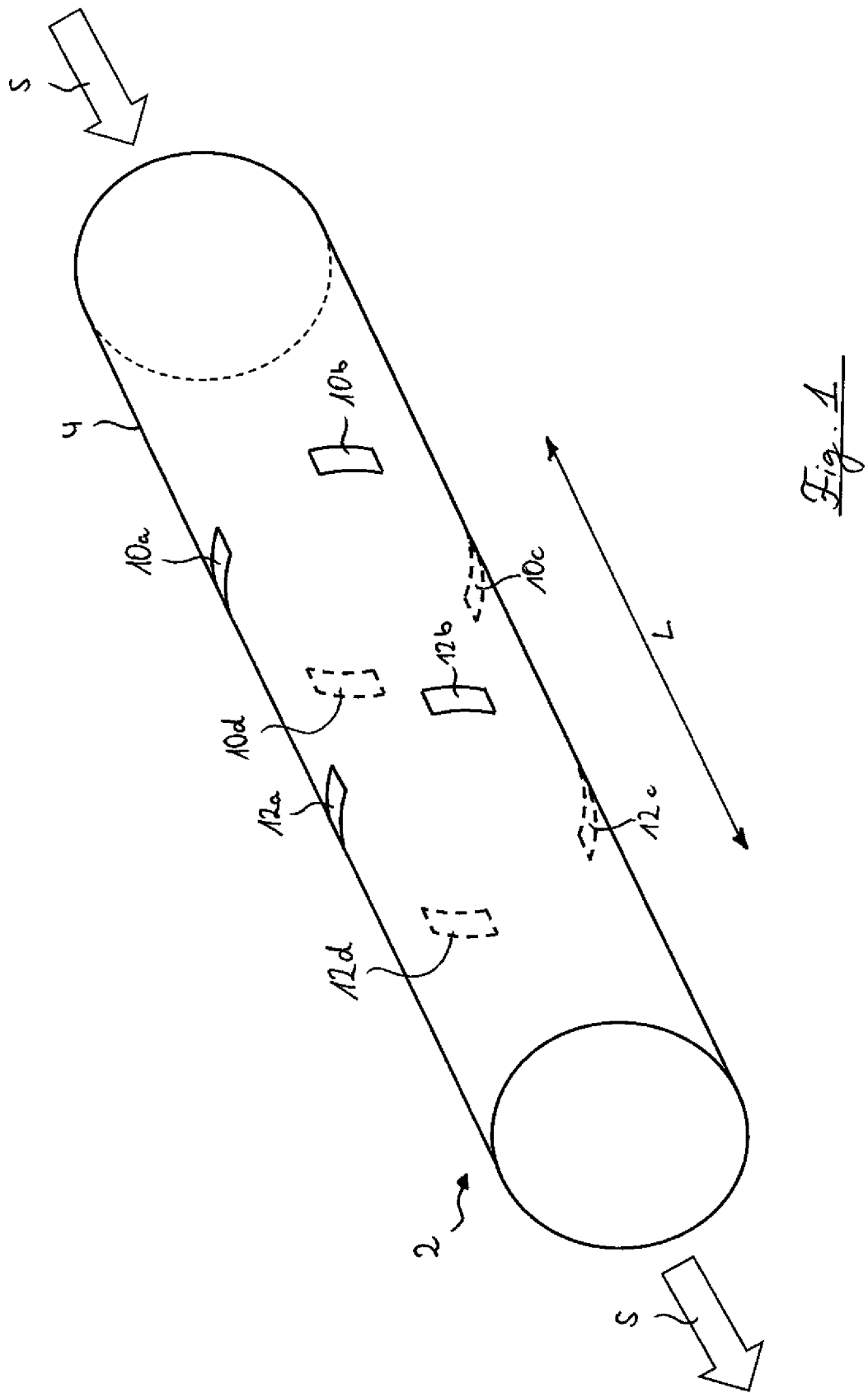
FIG. 1 shows a set-up of EMAT transducers according to the invention.

FIG. 1 shows a transducer set-up as part of a device for non-invasively determining properties of a multiphase flow, said transducer set-up being arranged on an electrically conductive, tubular object 2, through which the multiphase flow (not shown) flows along the main flow direction S. In this case, the device has four EMAT transducers 10a, 10b, 10c, 10d positioned upstream along a first object cross-section at or near the object wall 4, wherein one converter is respectively arranged at the 12 o'clock, 3 o'clock, 6 o'clock and 9 o'clock positions. Furthermore, the device has four EMAT transducers 12a, 12b, 12c, 12d positioned downstream along a second object cross-section at or near the object wall 4, wherein one converter in each case is arranged in a 12 o'clock, 3 o'clock, 6 o'clock and 9 o'clock position. The positions of the transducers 10a, 10b, 10c, 10d positioned upstream are varied relative to the positions of the transducers 12a, 12b, 12c, 12d positioned downstream only in the longitudinal direction L of the object 2. In each case two of the transducers 10a, 10b, 10c, 10d positioned upstream and in each case two of the transducers 12a, 12b, 12c, 12d positioned downstream are arranged diametrically opposite one another on the object 2. The transducers 10a, 10b, 10c, 10d, 12a, 12b, 12c, 12d are preferably configured both for transmission and for reception. In particular, the transducers 10a, 10b, 10c, 10d, 12a, 12b, 12c, 12d are embodied as phased array transducers (see FIG. 17).

Figure 2:
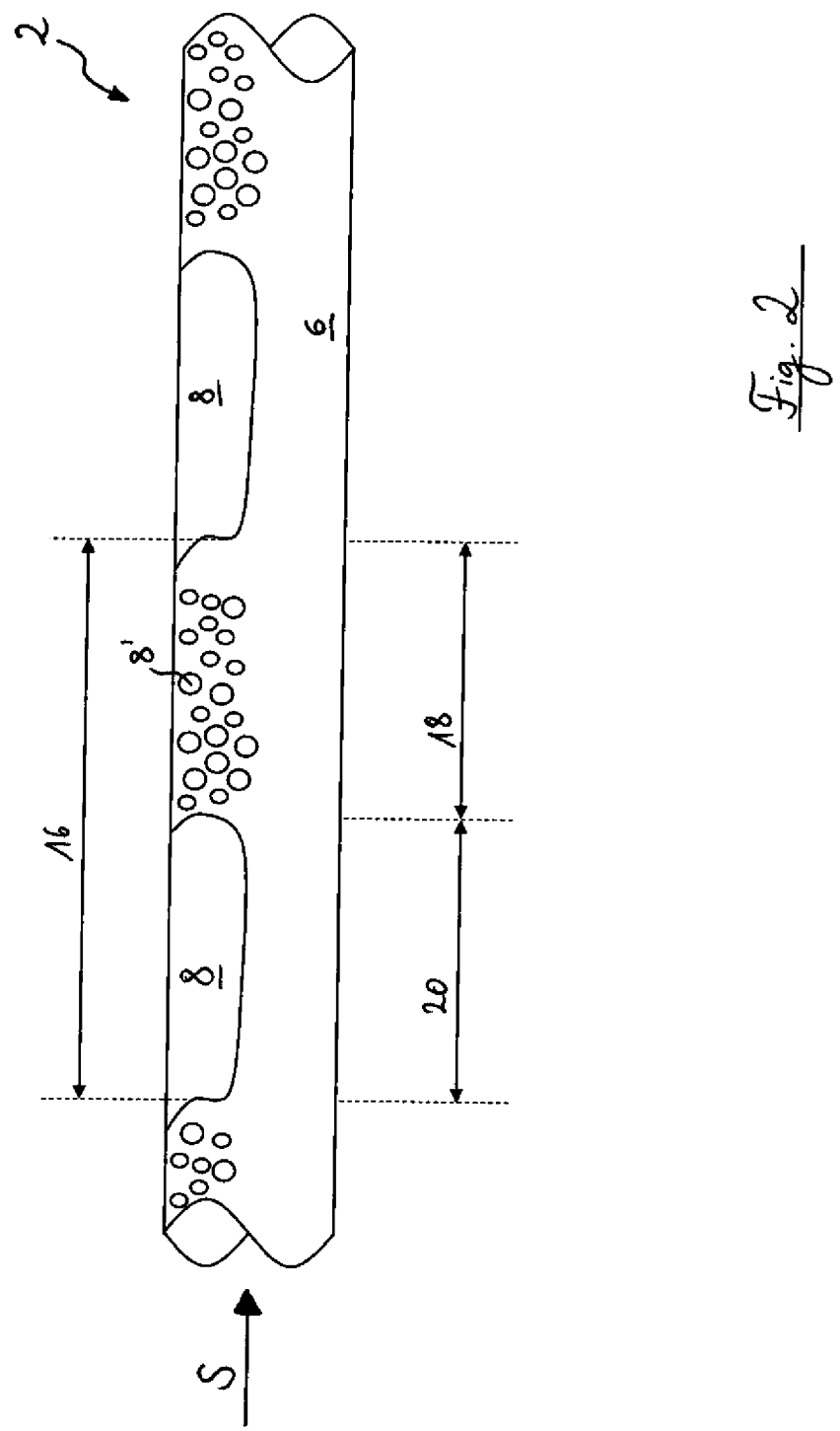
FIG. 2 shows a basic illustration of slug flow through a tubular object.

FIG. 2 shows a schematic illustration of so-called slug flow through the object 2. In this case, the multiphase flow comprises a liquid fraction 6 and a gaseous fraction, which is transported predominantly in the form of large Taylor bubbles 8 and here and there in the form of small gas voids 8'. The phase boundaries between the gaseous fraction and the liquid fraction 6 form reflection sources at which waves coupled into the multiphase flow can be reflected. Smaller gas voids 8' can occur not just in the region between two Taylor bubbles 8, but rather in the entire volume of the liquid fraction 6. A slug 18 and a Taylor bubble section 20 following it jointly form a slug cycle 16.

Figure 3:
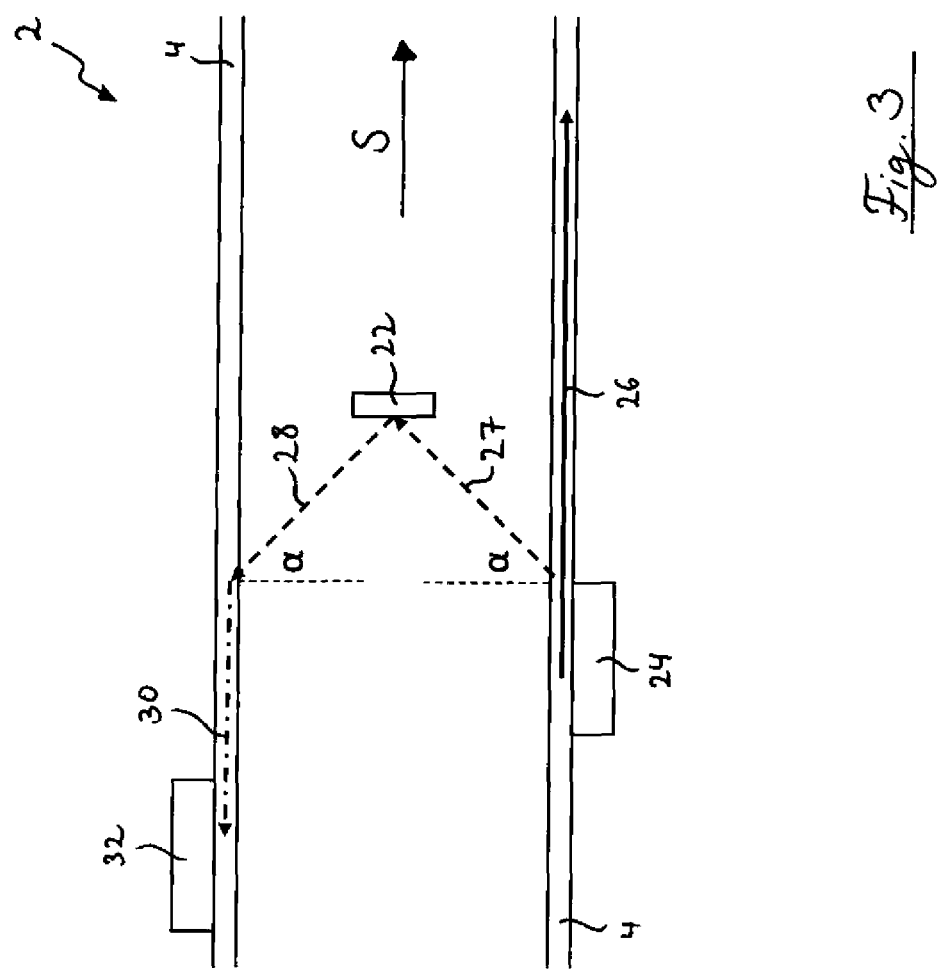
FIG. 3 shows one embodiment of the invention.
Figure 4:
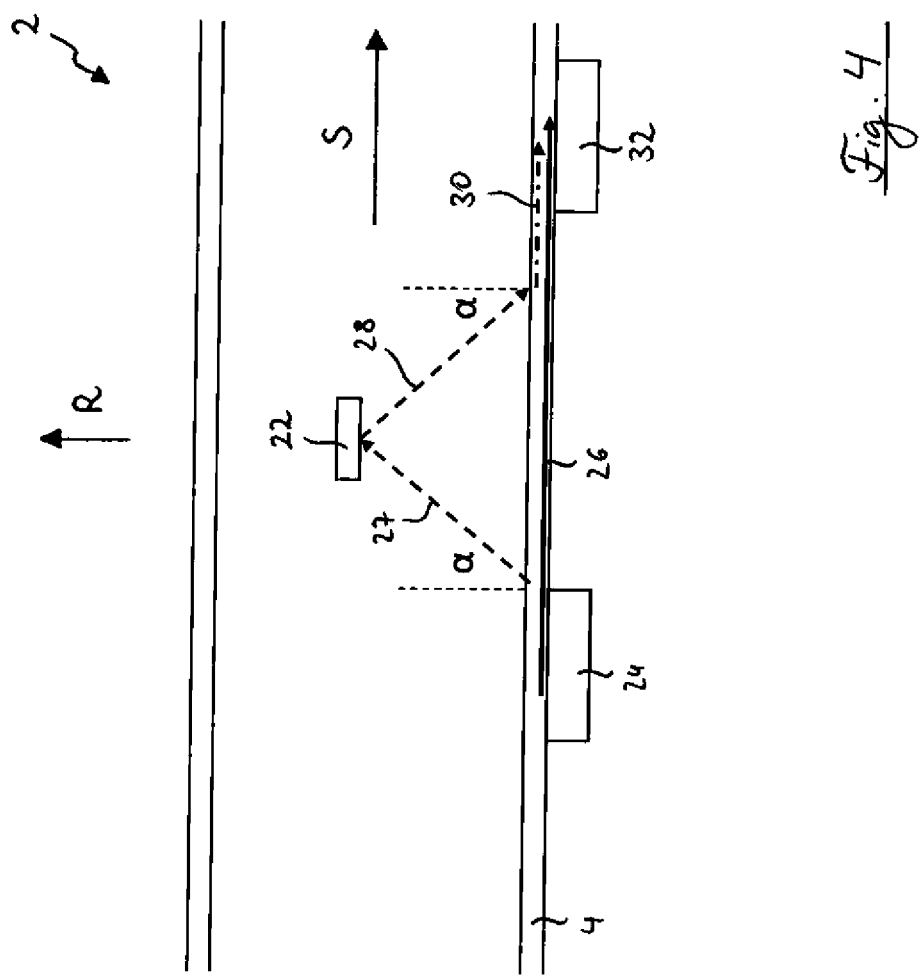
FIG. 4 shows a further embodiment of the invention.
Figure 5:
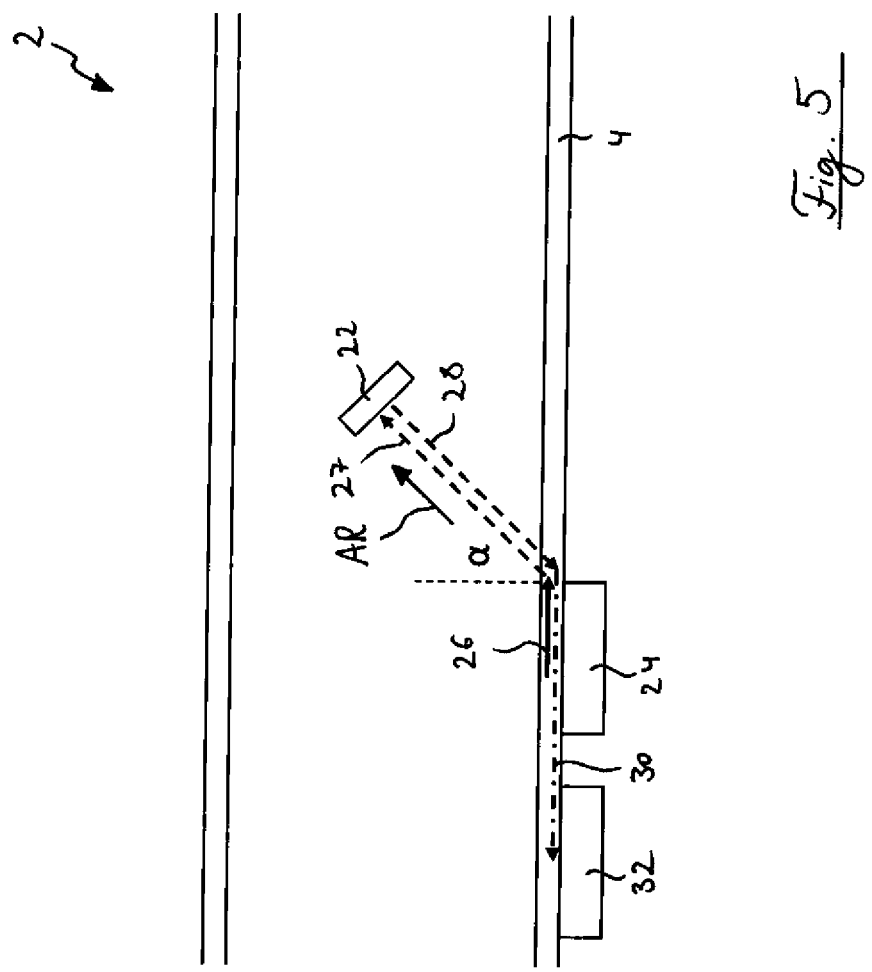
FIG. 5 shows a further embodiment of the invention.

FIGS. 3 to 5 show exemplary embodiments in which, for determining the velocity of the liquid fraction, signals arising on the basis of a wave 28 reflected from a reflection source 22 in the multiphase flow are evaluated. A transmission transducer 24 arranged at or near the object wall 4 on a first side of the object 2 generates a wave 26 that propagates axially in the object wall 4, wherein a part of the wave 26 couples into the multiphase flow at an angle α. The wave 27 coupled into the multiphase flow impinges on the reflection source 22 in the multiphase flow. The wave 28 reflected at the reflection surface couples into the object wall 4 at the entrance angle α and generates there a wave 30 in the object wall 4. A signal arising on the basis of this wave 30 generated in the object wall 4 is received by a reception transducer 32. In particular, the waves 26 in the object wall 4 are Lamb waves.

FIG. 3 shows an embodiment in which the reflection source 22 has a reflection surface extending perpendicular to the main flow direction S of the multiphase flow. The reflected wave 28 couples into the object wall 4 on the opposite side with respect to the transmission transducer 24, where a reception transducer 32 receives a corresponding signal.

Information regarding the velocity of the reflection source 22 can be obtained from said signal. In particular, small reflection sources 22 in the liquid fraction 6 of the multiphase flow that are attributed for example to smaller gas voids 8', drops of oil in the water or drops of water in the oil move concomitantly with the liquid fraction 6, with the result that the velocity of the liquid fraction 6 can be ascertained from the velocity of such reflection sources 22.

Preferably, periodically and for a specific period of time, waves (wave pulses) are generated and the signals arising on the basis of reflected waves 28 are evaluated. If the reflection source 22 moves in the direction of the main flow direction S of the multiphase flow, the time interval between the transmission of the wave 26 and the reception of the signal arising on the basis of the wave 30 increases. From a shift in the temporal position of a signal attributed to a specific reflection source 22, conclusions about the axial velocity of the reflection source 22 are drawn.

FIG. 4 shows an exemplary embodiment similar to FIG. 3 with a reflection source 22, the reflection surface of which extends parallel to the main flow direction S of the multiphase flow. A corresponding signal is received by a reception transducer 32 arranged on the same side as the transmission transducer 24. If the reflection source 22 moves perpendicular to the main flow direction S of the multiphase flow or in a radial direction R of the tubular object 2, from a shift in the temporal position of the signal attributed to the reflection source 22 it is possible to draw conclusions about the radial velocity of the reflection source 22.

FIG. 5 shows an exemplary embodiment similar to FIG. 3 and FIG. 4 with a reflection source 22 having a reflection surface extending perpendicular to the main propagation direction AR of the wave 27 coupled into the multiphase flow. The reflected wave 28 is reflected back by 180° relative to the wave 27 coupled into the multiphase flow. The velocity of said reflection source 22 has an axial and a radial velocity component. The signal arising from the wave 30 coupled into the object wall 4 is received by a reception transducer 32 on the same side of the object 2. In a further embodiment of the invention, the transmission transducer 24 is also configured for receiving the signal.

Figure 6:
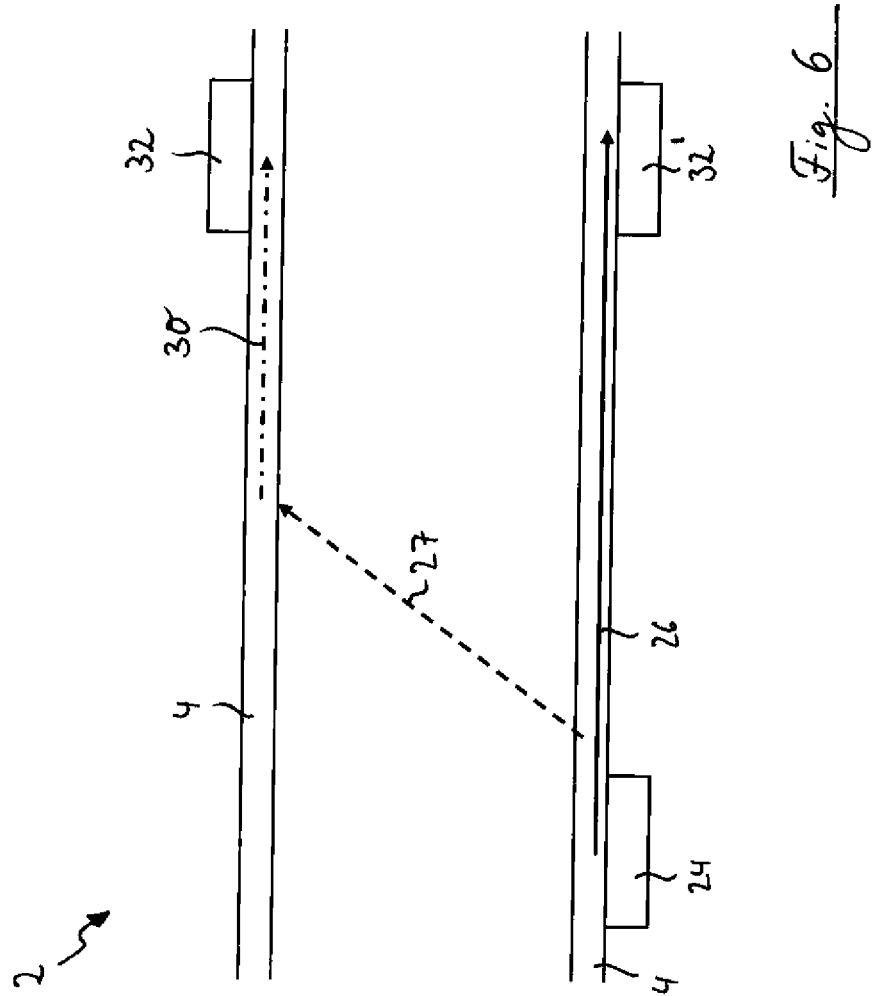
FIG. 6 shows a further embodiment of the invention.

FIG. 6 schematically shows the sequence of a propagation time measurement by means of a wave 27 coupled at least into a part of the multiphase flow. A transmission transducer 24 arranged at or near the object wall 4 on a first side of the object 2 generates a wave 26 that propagates axially in the object wall 4. A part of said wave 26 couples into the multiphase flow. The wave 27 coupled into at least part of the multiphase flow crosses the multiphase flow and couples into the object wall 4 on the opposite side and generates there a wave 30 in the object wall 4. From the time interval between the transmission of the wave 26 and the reception of the signal arising on the basis of the wave 30 by a reception transducer 32 arranged on the opposite side, in one embodiment of the invention, the sound velocity of the medium is ascertained. Preferably, the sound velocity of the liquid fraction 6 is ascertained in this case. With knowledge of the sound velocities of the individual components of the liquid fraction 6, i.e. of the water and/or of the hydrocarbon-containing liquid, it is possible to ascertain the respective fraction of the component and thus the water content in the liquid fraction itself.

For calculating the propagation time, a signal arising on the basis of that part of the transmitted wave 26 which propagates exclusively in the object wall 4 (direct wall signal) is used as reference. Said signal is received by a further reception transducer 32' on the same side on which the transmission transducer 24 is arranged.

Preferably, the wave 27 crossing the multiphase flow has a propagation path extending between a 3 o'clock position and a 9 o'clock position. Said path extends in particular in a plane extending substantially transversely with respect to the direction of gravitation. This increases the probability of the wave 27 crossing the liquid fraction 6 since, for most types of flow, the majority of the gaseous fraction collects in an upper region of the object 2 (10 o'clock position to 2 o'clock position).

From carrying out a propagation time measurement in accordance with FIG. 6 both downstream and upstream, in accordance with a further embodiment of the invention a propagation time difference between the signals measured upstream and downstream is ascertained, the velocity of the liquid fraction being determined from this difference. This is realized in a further embodiment according to the invention by an arrangement of two transducers 10b, 10d arranged upstream on opposite sides of the object and two transducers 12b, 12d arranged downstream on two opposite sides of the object.

Figure 7:
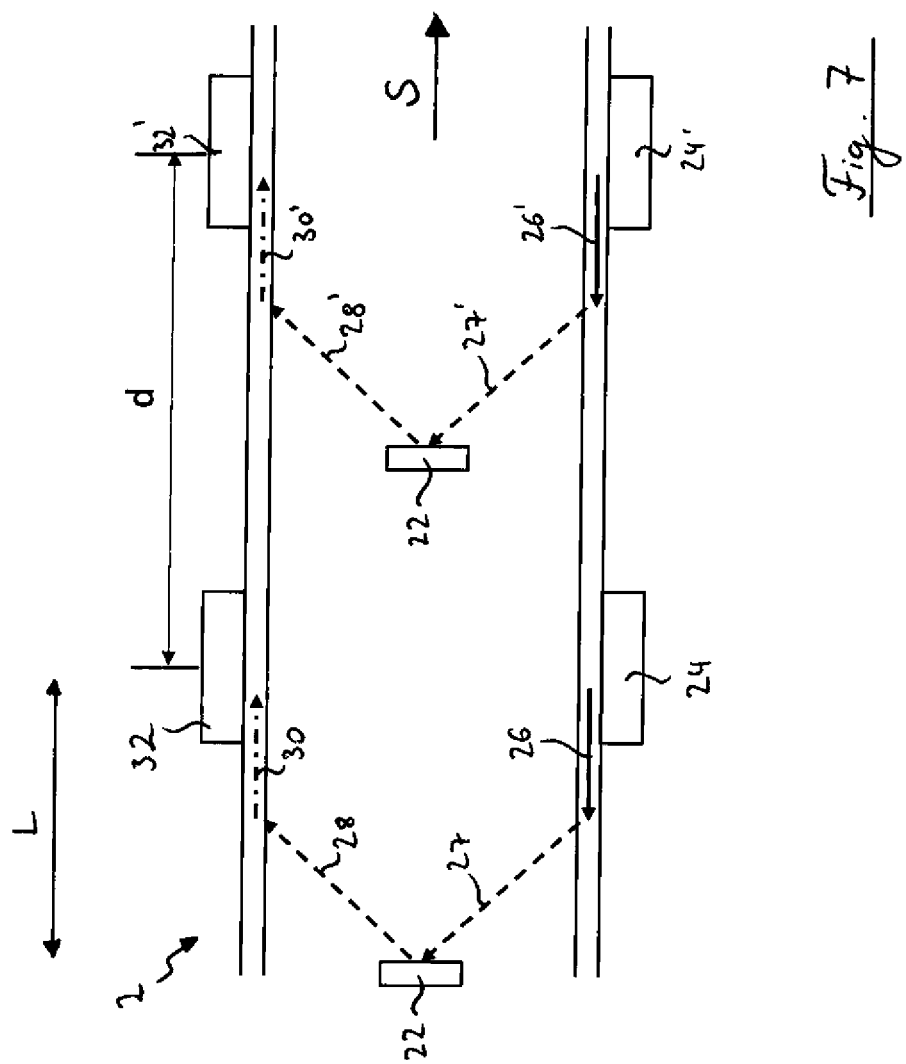
FIG. 7 shows a further embodiment of the invention.

FIG. 7 shows an exemplary embodiment according to the invention in which, for determining the velocity of the gaseous fraction, two signals are spatially correlated with one another. Along a first object cross-section, a transmission transducer 24 and a reception transducer 32 are arranged opposite one another. Along a second object cross-section, which is spaced apart from the first object cross-section by the distance d in the longitudinal direction L of the object 2, there are arranged a further transmission transducer 24' and a further reception transducer 32'. By way of example, a signal that arises on the basis of a wave 28 reflected at a reflection source 22 is observed at the first object cross-section. After a certain time, the same or a similar signal is observed at the second object cross-section. The velocity of the reflection source 22 can be determined from the distance d and the time that elapsed between the observations.

Figure 8:
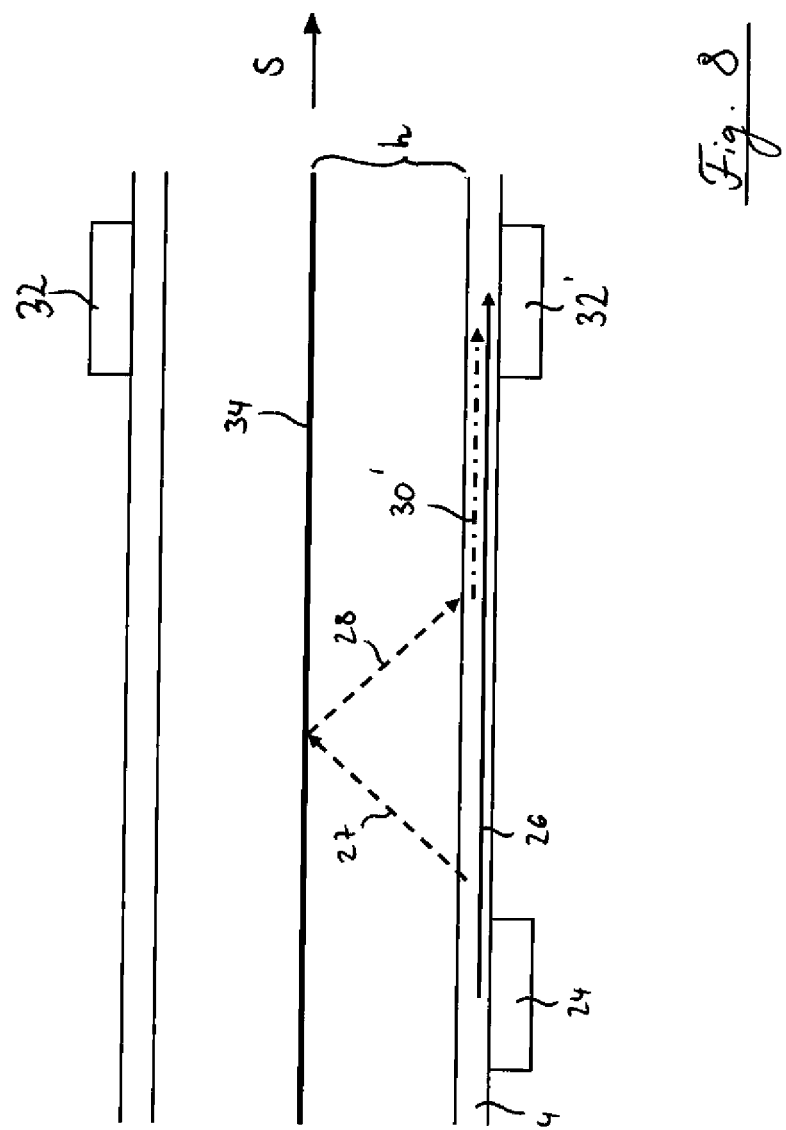
FIG. 8 shows a further embodiment of the invention.
Figure 9:
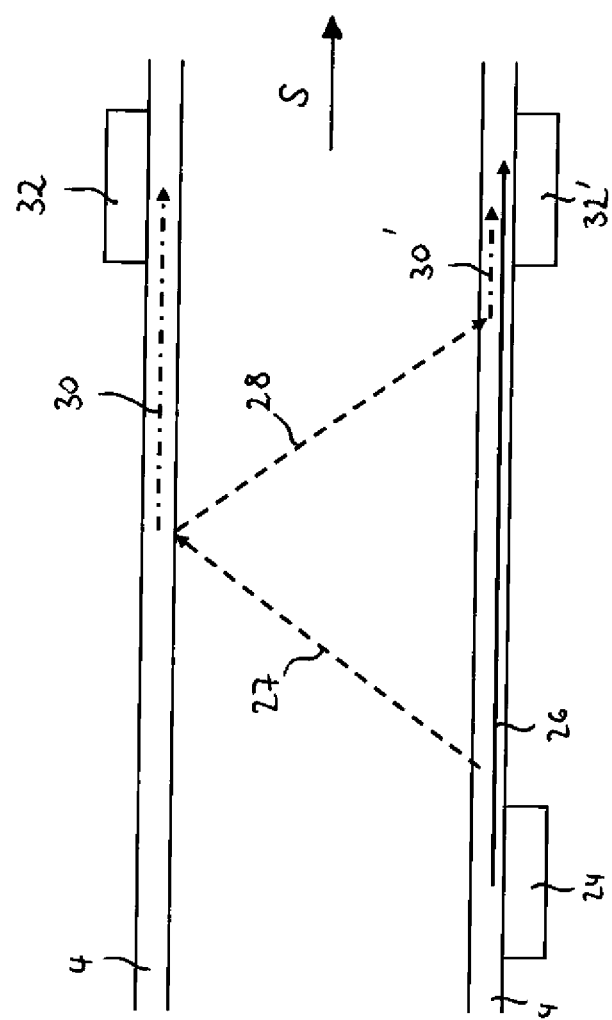
FIG. 9 shows a further embodiment of the invention.

The determination of the flow cross-section fraction of the gaseous fraction on the basis of a wave 27 transmitted downstream or upstream and coupled at least into a part of the multiphase flow is explained with reference to FIGS. 8 and 9. A transmission transducer 24 arranged in a bottommost position (6 o'clock position) at or near the object wall 4 generates a wave 26 that propagates axially in the object wall 4, wherein a part of the wave couples into the multiphase flow at a specific angle. Depending on the flow cross-section fraction of the gaseous fraction, the wave 27 coupled into the multiphase flow either is reflected at a horizontal phase boundary 34 extending parallel to the main flow direction S of the multiphase flow (FIG. 8) or crosses the multiphase flow at least once (FIG. 9). In one embodiment according to the invention, the flow cross-section fraction of the gaseous fraction is determined by way of the height h of the horizontal phase boundary 34. The height h is calculated in particular from the propagation time of a signal arising on the basis of the wave 28 reflected at the reflection surface, said signal being received by a reception transducer 32' arranged at a bottommost position (6 o'clock position). Preferably, larger gas bubbles in the multiphase flow, in particular Taylor bubbles 8 when slug flow is present, are detected in this way. In particular, for calculating the propagation time, a signal arising on the basis of a part of the transmitted wave 26 that propagates exclusively in the object wall (direct wall signal) is used as reference.

For the case where the multiphase flow consists substantially (at least apart from small gas voids 8') of liquid fraction 6 along at least one propagation path of the wave 27 coupled into the multiphase flow, the wave 27 can cross the multiphase flow and couple in on the opposite side of the object wall 4 (FIG. 9). In this case, a signal arising on the basis of the wave 27 crossing the multiphase flow is received by a reception transducer 32 arranged at a topmost position (12 o'clock position) at or near the object wall 4. For the case where the multiphase flow consists of liquid fraction 6 along a larger longitudinal section of the object 2, the wave 27 coupled into the multiphase flow from a first side of the object wall 4 can cross said multiphase flow twice, wherein the wave is reflected from the opposite side of the object wall 4 (reflected wave 28) and couples into the object wall 4 on the first side thereof, where it generates a wave 30' in the object wall 4. A signal arising from said wave 30' is received by the reception transducer 32'.

Figure 10:
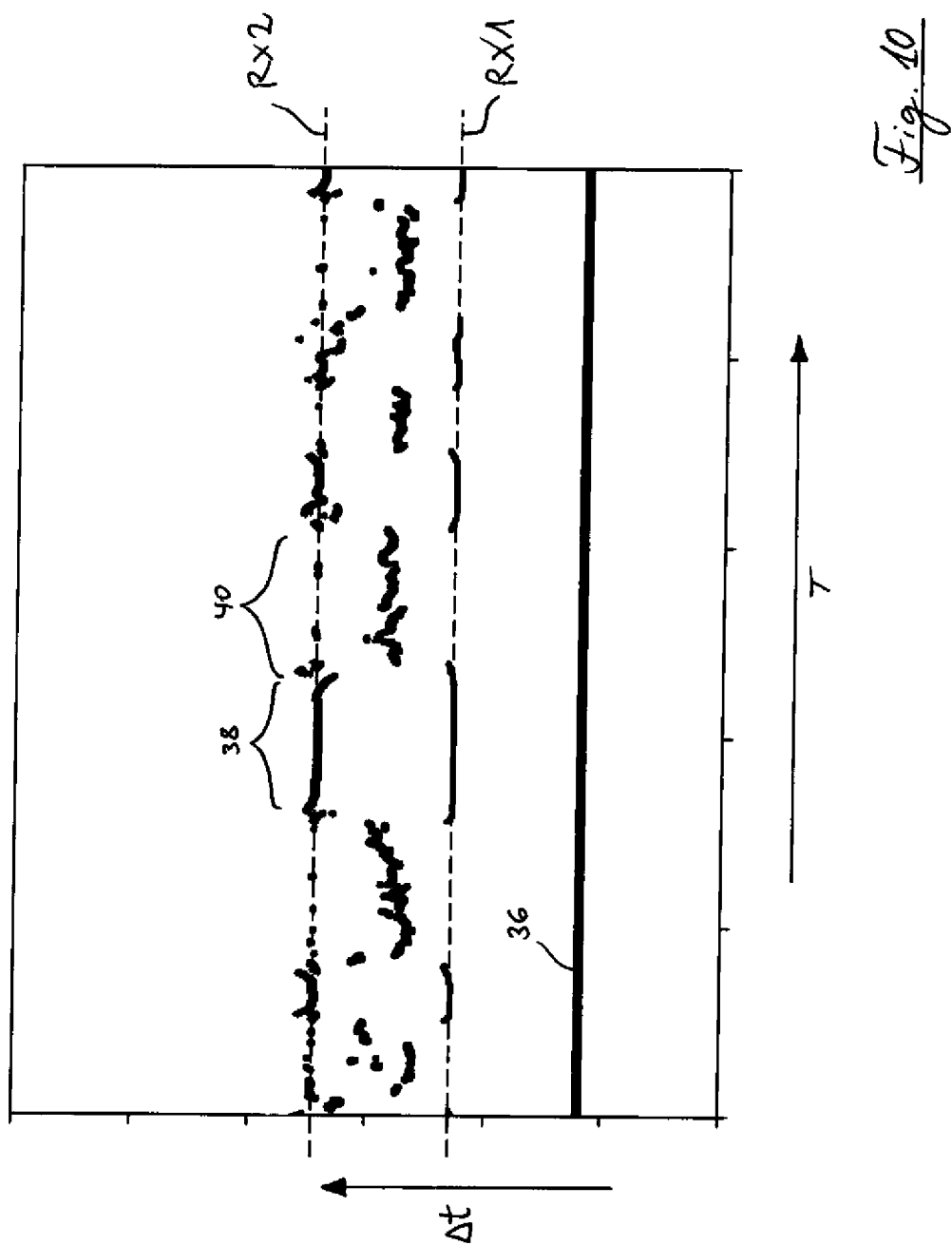
FIG. 10 shows a diagram with measurement results in accordance with the embodiments from FIGS. 8 and 9.
Figure 42:
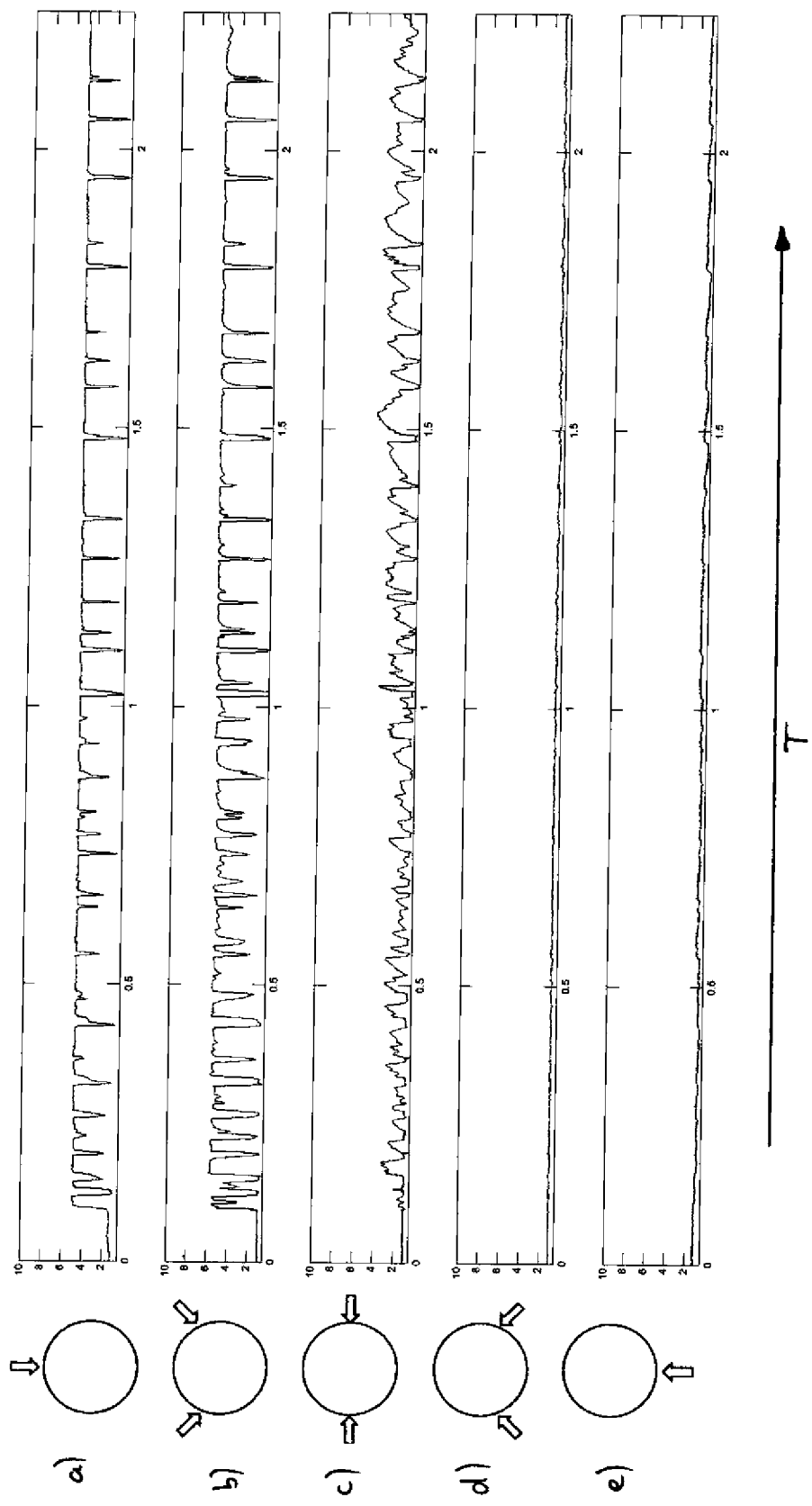

FIG. 10 illustrates the signals recorded repeatedly by the reception transducers 32, 32' over a relatively long period of time in accordance with the propagation time $\Delta t$ of said signals. The reception transducer 32' arranged at the bottommost position (6 o'clock position) firstly receives the direct wall signal 36, which is used in particular as reference for calculating the propagation times $\Delta t$. The reception transducer 32 arranged at the topmost position (12 o'clock position) receives a signal exclusively if, along a propagation path of the wave 27 coupled into the multiphase flow, the flow cross-section is completely occupied by the liquid fraction 6 of the multiphase flow. These signals are illustrated along the line RX1. If the wave 27 coupled into the multiphase flow can cross the latter twice, the reception transducer 32' arranged at the 6 o'clock position also receives a corresponding signal, characterized in particular by the maximum possible propagation time $\Delta t$. Such signals are illustrated along the line RX2. Signals that are reflected at the horizontal phase boundary 34 and are received by the reception transducer 32' arranged at the 6 o'clock position are situated between the lines RX1 and RX2. It is evident that over time T transmission regions 38 indicating a slug 18, in particular, and reflection regions 40 indicating a Taylor bubble section 20, in particular, follow one another cyclically. The measured propagation times $\Delta t$ at a specific time T provide information about the height of the horizontal phase boundary and thus about the flow cross-section fraction of the gaseous fraction.

A further method for determining the flow cross-section fraction of the gaseous fraction on the basis of a part of a wave transmitted downstream or upstream, said part propagating exclusively in the object wall, is described below with reference to FIGS. 11 and 12.

FIG. 11 shows a tubular object with a fully circumferential transmission transducer 42 arranged along a first object cross-section at or near the object wall 4, said transmission transducer transmitting upstream a wave fully circumferentially into the object wall, wherein the signals arising on the basis of that part of said wave which propagates exclusively in the object wall 4, at a second object cross-section spaced apart from the first object cross-section in the longitudinal direction L of the object 2, are received at different circumferential positions by eight reception transducers 44a to 44h arranged along the circumference.

The wave generated in the object wall 4 couples into the multiphase flow with different degrees of success depending on the composition of that part of the multiphase flow which adjoins the object wall 4, in particular depending on the density in said part. As becomes clear from FIG. 12, conclusions about the composition of that part of the multiphase flow which adjoins the object wall 4 can be drawn from the attenuation of the amplitude. FIG. 12 shows the profile of the amplitudes over time T of signals arising on the basis of that part of the transmitted wave which propagates exclusively in the object wall 4, which signals were received at different circumferential positions of the object. Diagram e) shows the evaluation of the signals received at a 6 o'clock position. The amplitude of the direct signal is relatively small since a large part of the wave coupled into that part of the multiphase flow which is situated behind the part of the object wall 4. The conclusion can be drawn from this that that part of the multiphase flow which is situated behind the part of the object wall 4 has a relatively high density, that is to say belongs in particular to the liquid fraction 6 of the multiphase flow. The same applies to diagram d), in which a similar signal was measured at the 4 o'clock position and the 8 o'clock position.

By contrast, signals received at the 12 o'clock position are evaluated in diagram a). The amplitude stays on a plateau over extensive portions. This indicates that for the majority of the time a part of the multiphase flow having a lower density, in particular the gaseous fraction, is present behind the corresponding part of the object wall 4. The recurring values or dips in amplitude are attributable to the fact that at these points in time the flow cross-section is occupied by a part of the multiphase flow having a relatively high density, in particular the liquid fraction 6. A similar situation can be observed in diagram b) (2 o'clock and 10 o'clock positions). In diagram c), where signals received at a 3 o'clock and a 6 o'clock position were evaluated, the amplitude fluctuates the most, which indicates that liquid and gaseous fraction occur alternately behind the corresponding parts of the object wall 4.

Figure 13:
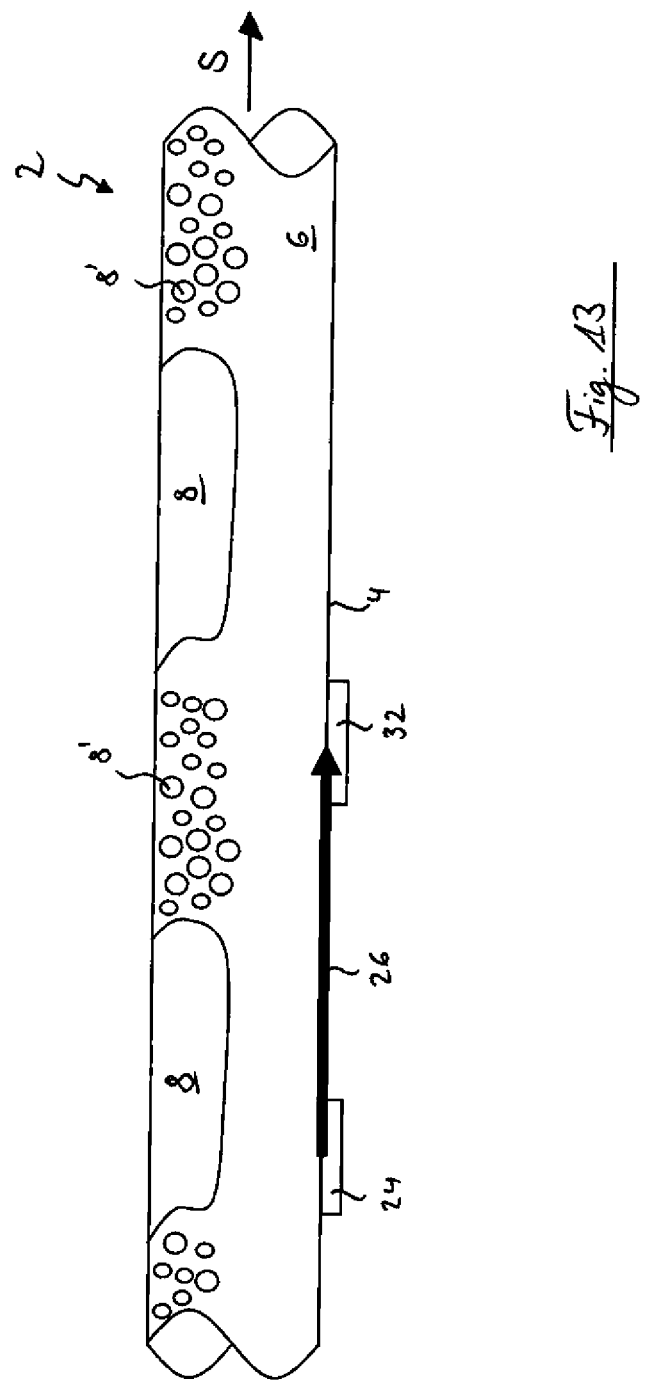
FIG. 13 shows a transducer set-up of a further embodiment of the invention

The embodiment according to the invention according to FIG. 13 shows a signal arising on the basis of a part of a wave transmitted by a transmission transducer 24 arranged in a 6 o'clock position, said part propagating exclusively in the object wall 4, for determining the water content in the liquid fraction 6 of the multiphase flow. The signal received by the reception transducer 32 is plotted in accordance with its amplitude over time in the diagram shown in FIG. 14. In this case, the measurement curve A1 corresponds to a water fraction of 0%, the measurement curve A2 corresponds to a water fraction of 20% and the measurement curve A3 corresponds to a water fraction of 100%. The proportion of the total flow phase made up of the flow rate of the gaseous fraction was 33% in all three measurements.

FIG. 15 shows a flexible carrier 46, embodied in particular as a printed circuit board, with four transducers 48 to be arranged along an object cross-section. The transducers 48 can thus be positioned optimally at the outer contour of the object wall 4, the positioning of the transducers with respect to one another (12 o'clock, 3 o'clock, 6 o'clock and 9 o'clock positions) being predefined, which makes the installation of the device more practical. In a further embodiment according to the invention in accordance with FIG. 16, in a flexible carrier 46 embodied in particular as a printed circuit board, besides a transducer 50 encompassing the object 2 substantially fully circumferentially, in addition there are arranged eight transducers 48 that in their entirety substantially cover the object 2 in a circumferential direction.

FIG. 17 schematically shows a construction of a transducer 48 embodied as a phased array transducer and comprising two mutually offset coils 52, 54, which are offset spatially by $\lambda/4$ with respect to one another, wherein $\lambda$ is the wavelength of the wave 26 generated in the object wall 4. By virtue of the spatial offset in combination with a corresponding phase offset of the excitation currents of 90°, it is possible to transmit the wave 26 in the object wall 4 (not shown) directionally in direction W or in direction W'—depending on the sign of the phase offset.

The invention claimed is:

1. A method for non-invasively determining properties of a multiphase flow which comprises a liquid fraction and a gaseous fraction and flows through an electrically conductive object, the method using a single set-up having a plurality of EMAT transducers, the method comprising the steps of:
    determining the velocity of the gaseous fraction by spatially correlating at least two signals with one another;
    determining the velocity of the liquid fraction by evaluating:
        at least one signal arising on the basis of a wave reflected from a reflection source in the multiphase flow, or
        at least one signal arising on the basis of a wave transmitted upstream and coupled at least into a part of the multiphase flow and at least one signal arising on the basis of a wave transmitted downstream and coupled at least into a part of the multiphase flow; and
    determining at least one of the flow cross-section fraction of the gaseous fraction and the flow cross-section fraction of the liquid fraction by evaluating:
        at least one signal arising on the basis of a wave transmitted downstream or upstream and coupled at least into a part of the multiphase flow, or
        at least one signal arising on the basis of a part of a wave transmitted downstream or upstream, said part propagating exclusively in the object wall.

2. The method of claim 1, wherein at least the flow rate of the liquid fraction and/or the flow rate of the gaseous fraction are/is ascertained from at least two properties of the multiphase flow.

3. The method according to claim 1, further including determining the water content in the liquid fraction by evaluating at least one of at least one signal arising on the basis of a part of a wave transmitted downstream or upstream, said part propagating exclusively in the object wall, and at least one signal arising on the basis of a wave transmitted upstream or downstream and coupled at least into a part of the multiphase flow.

4. The method according to claim 3, further including determining the water content in the liquid fraction by evaluating at least one signal arising on the basis of a wave transmitted upstream or downstream and coupled at least into a part of the multiphase flow and a signal arising on the basis of a further wave transmitted in the respective other direction (upstream or downstream) and coupled at least into a part of the multiphase flow.

5. The method according to claim 1, wherein for determining the flow cross-section fraction of the gaseous fraction and/or for determining the water content in the liquid fraction, the at least one signal arising on the basis of a part of a wave transmitted upstream or downstream at a first position, said part propagating exclusively in the object wall, is received at a second position, which is spaced apart from the first position in the longitudinal direction (L) of the object, wherein the composition of that part of the multiphase flow which adjoins the object wall is ascertained on the basis of the amplitude (A) of the signal.

6. The method according to claim 1, wherein when the object extends horizontally, at least one portion of the waves transmitted upstream and/or downstream and coupled at least into a part of the multiphase flow has in each case at least one propagation path extending between a 3 o'clock position and a 9 o'clock position.

7. The method according to claim 1, wherein for determining the velocity of the gaseous fraction, at least two signals at two positions spaced apart from one another in the longitudinal direction (L) of the object are correlated with one another.

8. The method according to claim 1, wherein for determining the velocity of the liquid fraction and/or the velocity of the gaseous fraction, a frequency shift of the signal arising on the basis of a wave reflected from a reflection source in the multiphase flow is evaluated.

9. The method according to claim 1, wherein for determining the velocity of the liquid fraction, periodically waves are generated and the signals arising on the basis of reflected waves are evaluated, wherein, from a shift of the temporal position of at least one signal attributed to a specific reflection source, at least the velocity of the reflection source is ascertained.

10. The method according to claim 1, wherein for determining the velocity of the liquid fraction, at least one signal arising on the basis of a wave reflected from a reflection surface extending perpendicular or parallel to the main flow direction (S) of the multiphase flow or perpendicular to the main propagation direction (AR) of the wave coupled into the multiphase flow is evaluated.

11. The method according to claim 1, wherein for determining the velocity of the liquid fraction, the propagation time difference between the at least one signal arising on the basis of the wave transmitted upstream and coupled into at least one part of the multiphase flow and the at least one signal arising on the basis of the wave transmitted downstream and coupled into at least one part of the multiphase flow is evaluated.

12. The method according to claim 1, wherein for determining the flow cross-section fraction of the gaseous fraction, at least one signal arising on the basis of a wave reflected from a reflection source in the multiphase flow, said wave arising at least partly from the wave transmitted upstream or downstream at a first position and coupled into at least one part of the multiphase flow, is received at a second position, which is spaced apart from the first position in the longitudinal direction (L) of the object.

13. The method according to claim 12, wherein the wave transmitted downstream or upstream at a first position is transmitted from a deepest circumferential position (6 o'clock position) and the signal arising on the basis of the wave reflected from a reflection source in the multiphase flow is received at a deepest circumferential position (6 o'clock position).

14. The method according to claim 1, wherein for determining the flow cross-section fraction of the gaseous fraction, at least one signal arising on the basis of a wave transmitted through at least one part of the multiphase flow is evaluated, wherein the transmitted wave arises at least partly from the wave transmitted into the multiphase flow downstream or upstream.

15. The method according to claim 1, wherein for determining the flow cross-section fraction of the gaseous fraction, at least one signal arising from a wave transmitted twice through at least one part of the multiphase flow is evaluated, wherein the wave transmitted twice arises at least partly from the wave transmitted into the multiphase flow downstream or upstream.

16. The method according to claim 1, wherein for determining the flow cross-section fraction of the gaseous fraction, the at least one wave transmitted upstream or downstream is transmitted into the object wall fully circumferentially along a first object cross-section and the signals arising on the basis of that part of said wave which propagates exclusively in the object wall, at a second object cross-section spaced apart from the first object cross-section in the longitudinal direction (L) of the object, are received at at least two different circumferential positions.

17. The method according to claim 1, wherein at least one of the measurement methods is assigned specific configuration parameters on the basis of which the transducers used for the measurement method are controlled.

18. The method according to claim 1, wherein at least one of the transducers is used both as transmitter and as receiver.

19. The method according to claim 1, wherein at least one of the transducers transmits directionally upstream and/or downstream.

20. The method according to claim 1, wherein at least one of the transducers generates Lamb waves in the object wall.

21. The method according to claim 1, wherein for at least one property of the multiphase flow the measurement method determining it is selected depending on the ratio of gaseous fraction to liquid fraction of the multiphase flow.

22. The method according to claim 1, wherein for determining at least one of the properties for at least one measurement method a plurality of individual measurements are carried out and evaluated, wherein in particular preferably a mean value and/or a maximum value are/is ascertained.

23. The method according to claim 1, wherein for at least one measurement method a pulse repetition frequency of at least 200 Hz and a maximum of 5 kHz, is used.

24. A device for non-invasively determining properties of a multiphase flow which comprises a liquid fraction and a gaseous fraction and flows through an electrically conductive object, wherein the device is configured to perform the method according to claim 1, the device comprising:
at least four EMAT transducers positionable upstream along a first object cross-section at or near an object wall; and
at least four EMAT transducers positionable downstream along a second object cross-section at or near the object wall,
wherein respectively two of the transducers positionable upstream and respectively two of the transducers positionable downstream are arranged opposite one another on the object,
wherein the positions of the transducers positionable upstream are varied relative to the positions of the transducers positionable downstream only in the longitudinal direction (L) of the object;
a control unit, which controls the transducers used for the respective measurement method; and an evaluation unit which evaluates data generated from the signals received from the EMAT transducers.

25. The device according to claim 24, wherein at least the EMAT transducers arranged along one of the object cross-sections in their entirety at least substantially cover the object in a circumferential direction.

26. The device according to claim 24, wherein the device comprises along a first object cross-section and/or a second object cross-section in each case at least six EMAT transducers positionable at or near the object wall.

27. The device according to claim 24, wherein the device furthermore comprises at least one EMAT transducer encompassing the object substantially fully circumferentially.

28. The device according to claim 24, wherein the device comprises at least two EMAT transducers embodied fully circumferentially, wherein a first EMAT transducer embodied fully circumferentially is arranged upstream along a first object cross-section at or near the object wall, and a second EMAT transducer embodied fully circumferentially is arranged downstream of the at least four EMAT transducers positionable downstream along a second object cross-section at or near the object wall.

29. The device according to claim 24, wherein at least one of the transducers is embodied as a phased array transducer comprising at least two coils which are spatially offset with respect to one another.

30. The device according to claim 24, wherein in a radial direction (R) of the object above at least one first transducer configured for generating ultrasonic waves having a first wavelength ($\lambda$), there is arranged at least one further transducer configured for generating ultrasonic waves having a different wavelength ($\lambda$).

31. The device according to claim 24, wherein the device has at least one flexible carrier, in which are arranged the transducers positionable upstream and/or the transducers positionable downstream and/or the EMAT transducers embodied fully circumferentially.

32. The device according to claim 29, wherein the coils of at least one of the transducers are arranged one above another in a radial direction (R) of the object.

33. The device according to claim 29, wherein the coils of at least one of the transducers are printed on a flexible printed circuit board.

34. The method of claim 1 performed by a device comprising:

at least four EMAT transducers positionable upstream along a first object cross-section at or near an object wall; and at least four EMAT transducers positionable downstream along a second object cross-section at or near the object wall, wherein respectively two of the transducers positionable upstream and respectively two of the transducers positionable downstream are arranged opposite one another on the object, wherein the positions of the transducers positionable upstream are varied relative to the positions of the transducers positionable downstream only in the longitudinal direction (L) of the object;

a control unit, which on the basis of specific configuration parameters, controls the transducers used for the respective measurement method; and an evaluation unit which evaluates data generated from signals received from the EMAT transducers.

35. The method of claim 21, wherein for at least one property of the multiphase flow the measurement method determining it is selected depending on at least one of the flow rate of the liquid fraction and the flow rate of the gaseous fraction.

36. The method of claim 1, wherein the step of determining the velocity of the liquid fraction occurs by evaluating both:
the at least one signal arising on the basis of the wave reflected from the reflection source in the multiphase flow, and
the at least one signal arising on the basis of the wave transmitted upstream and coupled at least into a part of the multiphase flow and at least one signal arising on the basis of the wave transmitted downstream and coupled at least into a part of the multiphase flow.

37. The method of claim 1, wherein the step of determining at least one of the flow cross-section fraction of the gaseous fraction and the flow cross-section fraction of the liquid fraction occurs by evaluating both:
the at least one signal arising on the basis of the wave transmitted downstream or upstream and coupled at least into a part of the multiphase flow, and
the at least one signal arising on the basis of a part of the wave transmitted downstream or upstream, said part propagating exclusively in the object wall.

* * * * *